(12) United States Patent
Kikugawa et al.

(10) Patent No.: US 8,846,571 B2
(45) Date of Patent: Sep. 30, 2014

(54) HERBICIDAL COMPOSITIONS CONTAINING BENZOYLPYRAZOLE COMPOUNDS

(71) Applicant: Ishihara Sangyo Kaisha, Ltd., Osaka (JP)

(72) Inventors: Hiroshi Kikugawa, Kusatasu (JP); Souichiro Nagayama, Kusatsu (JP); Makiko Sano, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 0 days.

(21) Appl. No.: 13/910,562

(22) Filed: Jun. 5, 2013

(65) Prior Publication Data

US 2013/0338004 A1 Dec. 19, 2013

Related U.S. Application Data

(63) Continuation of application No. 13/133,993, filed as application No. PCT/JP2009/071004 on Dec. 10, 2009, now Pat. No. 8,492,310.

(30) Foreign Application Priority Data

Dec. 11, 2008 (JP) .................................. 2008-316203

(51) Int. Cl.
| | | |
|---|---|---|
| *A01N 43/40* | (2006.01) | |
| *A01N 43/64* | (2006.01) | |
| *A01N 43/60* | (2006.01) | |
| *A01N 43/36* | (2006.01) | |

(52) U.S. Cl.
USPC ............ 504/130; 504/134; 504/136; 504/138

(58) Field of Classification Search
None
See application file for complete search history.

(56) References Cited

U.S. PATENT DOCUMENTS

| | | | |
|---|---|---|---|
| 5,998,334 A | 12/1999 | Murai et al. | |
| 8,119,569 B2 * | 2/2012 | Komyoji et al. | 504/282 |
| 8,435,928 B2 * | 5/2013 | Kikugawa et al. | 504/244 |
| 8,466,089 B2 * | 6/2013 | Tsukamoto et al. | 504/282 |
| 8,492,310 B2 | 7/2013 | Kikugawa et al. | |
| 2009/0286683 A1 | 11/2009 | Shimoharada et al. | |
| 2010/0075855 A1 | 3/2010 | Komyoji et al. | |
| 2010/0099563 A1 | 4/2010 | Shimoharada et al. | |
| 2010/0197500 A1 | 8/2010 | Kikugawa et al. | |
| 2010/0317528 A1 | 12/2010 | Shimoharada et al. | |
| 2011/0160062 A1 | 6/2011 | Tsukamoto et al. | |
| 2011/0282070 A1 | 11/2011 | Shimoharada et al. | |

FOREIGN PATENT DOCUMENTS

| | | | |
|---|---|---|---|
| EP | 0 352 543 | | 1/1990 |
| EP | 2 103 215 | | 9/2009 |
| EP | 2 106 697 | | 10/2009 |
| JP | 2009 40771 | | 2/2009 |
| WO | 2008 065907 | | 6/2008 |
| WO | WO-2008065907 | * | 6/2008 |
| WO | 2008 093840 | | 8/2008 |

OTHER PUBLICATIONS

U.S. Appl. No. 13/880,599, filed Apr. 19, 2013, Kikugawa, et al.
International Search Report issued Apr. 7, 2010 in PCT/JP09/71004 filed Dec. 10, 2009.

* cited by examiner

*Primary Examiner* — Alton Pryor
(74) *Attorney, Agent, or Firm* — Oblon, Spivak, McClelland, Maier & Neustadt, L.L.P.

(57) ABSTRACT

[OBJECT]
To provide a novel pesticide.
[MEANS OF ACCOMPLISHING THE OBJECT]
The present invention provides a herbicidal composition which comprises as active ingredients (a) a herbicidal benzoylpyrazole compound represented by the formula (I) or its salt:

[KA 1]

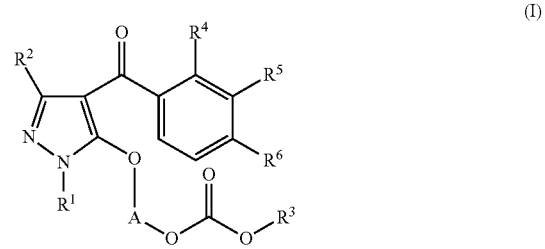

(I)

wherein $R^1$ is alkyl or cycloalkyl, $R^2$ is a hydrogen atom or alkyl, $R^3$ is alkyl, $R^4$ is alkyl, haloalkyl or the like, $R^5$ is a hydrogen atom, alkyl or the like, $R^6$ is haloalkyl, halogen or the like, and A is alkylene substituted by alkyl, and (b) other herbicidal compound.

9 Claims, No Drawings

HERBICIDAL COMPOSITIONS CONTAINING BENZOYLPYRAZOLE COMPOUNDS

CROSS REFERENCE TO RELATED APPLICATION

This application is a continuation application of U.S. patent application Ser. No. 13/133,993, filed on Jun. 10, 2011, which was a National Stage entry under 35 USC 371 of PCT/JP2009/071004, filed on Oct. 12, 2009, and claims priority to Japanese Patent Application No. 2008-316203, filed on Dec. 11, 2008.

TECHNICAL FIELD

The present invention relates to herbicidal compositions containing as active ingredients (a) a herbicidal benzoylpyrazole compound or its salt and (b) other herbicidal compound.

BACKGROUND ART

In Patent Documents 1 and 2, it is disclosed that certain pyrazole compounds are useful as herbicides, and some other herbicides which can be used as mixed with such compounds, are exemplified. Patent Document 3 discloses mixed use of certain pyrazole compounds with other herbicides. However, these documents do not specifically disclose a herbicidal composition comprising as active ingredients a herbicidal benzoylpyrazole compound represented by the following formula (I) and other herbicidal compound.

[PATENT DOCUMENT 1] EP352543A
[PATENT DOCUMENT 2] WO2008/065907
[PATENT DOCUMENT 3] WO2008/093840

DISCLOSURE OF THE INVENTION

Object to be Accomplished by the Invention

At present, many herbicidal compositions have been developed and used, but there are a variety of types of weeds to be controlled, and their development lasts for a long period of time. Thus, a high activity and long lasting herbicidal composition having a wider herbicidal spectrum has been desired. Further, in recent years, a technique to reduce the dose of the active ingredient has been desired so as to reduce the environmental load to a place where the herbicide is applied or a periphery thereof.

Means to Accomplish the Object

The present inventors have conducted extensive studies to accomplish the above object and as a result, found a highly useful herbicidal composition.

That is, the present invention relates to a herbicidal composition which comprises as active ingredients (a) a herbicidal benzoylpyrazole compound represented by the formula (I) or its salt (hereinafter referred to as compound Q):

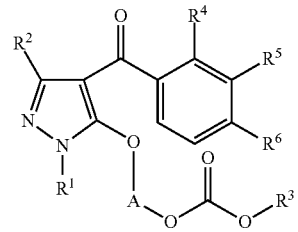

(I)

wherein $R^1$ is alkyl or cycloalkyl, $R^2$ is a hydrogen atom or alkyl, $R^3$ is alkyl, $R^4$ is alkyl; haloalkyl; alkoxy; halogen; nitro; cyano; alkylthio; alkylsulfinyl; or alkylsulfonyl, $R^5$ is a hydrogen atom; alkyl; alkenyl; alkynyl; halogen; cyano; cyanoalkyl; cyanoalkenyl; haloalkyl; alkoxyalkyl; haloalkoxyalkyl; amino(thiocarbonyl)alkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$; thiocyanatoalkyl; alkoxy; alkenyloxy; alkynyloxy; haloalkoxy; alkoxyalkoxy; haloalkoxyalkoxy; alkoxyhaloalkoxy; halo alkoxyhaloalkoxy; alkoxyalkoxyalkyl; alkylthio; alkoxyalkylthio; halo alkoxyalkylthio; alkoxyhaloalkylthio; haloalkoxyhaloalkylthio; alkylthioalkylthio; haloalkylthioalkylthio; alkylthiohaloalkylthio; haloalkylthiohaloalkylthio; alkylthioalkoxy; alkylsulfonyl; alkylsulfonylalkyl; alkoxycarbonylalkyl; alkoxycarbonylalkoxy; heterocyclylalkyl; heterocyclyloxy; heterocyclylalkoxy; heterocyclylalkoxyalkyl; heterocyclyloxyalkyl; cycloalkyloxy; —OC(O)SR$^7$; —OC(O)OR$^7$; —C(O)OR$^7$; —C(O)SR-7; —C(S)OR$^7$; —C(S)SR$^7$; or aminoalkyl which may be substituted by at least one substituent selected from alkyl, cyano, cyanoalkyl, (alkylthio)carbonylalkyl, alkyl(thiocarbonyl)alkyl, —C(O)OR$^7$ and —C(O)SR$^7$, $R^6$ is haloalkyl; halogen; nitro; cyano; alkylthio; alkylsulfinyl; or alkylsulfonyl, A is alkylene substituted by at least one alkyl, $R^7$ is alkyl; haloalkyl; alkoxyalkyl; alkenyl; haloalkenyl; alkynyl; or arylalkyl which may be substituted by $R^8$, and each of $R^8$ which is independent of one another, is halogen; alkyl; or alkoxy, and (b) other herbicidal compound. Further, the present invention relates to a method for controlling undesired plants, which comprises applying a herbicidally effective amount of the above herbicidal composition to the undesired plants or to a place where they grow. Further, the present invention relates to a method for controlling undesired plants, which comprises applying a herbicidally effective amount of the compound Q and a herbicidally effective amount of other herbicidal compound to the undesired plants or to a place where they grow.

Effects of the Invention

The herbicidal composition of the present invention, i.e. the herbicidal composition comprising as active ingredients the compound Q and other herbicidal compound, is capable of controlling a wide range of undesired plants emerging in agricultural fields or non-agricultural fields. It surprisingly presents a synergistic herbicidal effect i.e. a herbicidal effect higher than the mere addition of the respective herbicidal effects of the active ingredients. Such a herbicidal composition of the present invention can be applied at a low dose as compared with a case where the respective active ingredients are applied individually. Thus, it is effective to reduce the environmental load on a place where the composition is applied or a periphery thereof. Further, the herbicidal spectrum will be enlarged, and further the herbicidal effects will last over a long period of time.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E=\alpha+\beta-(\alpha\times\beta\div100)$$

where

α: growth inhibition rate when treated with x (g/ha) of herbicide X,

β: growth inhibition rate when treated with y (g/ha) of herbicide Y,

E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

BEST MODE(S) FOR CARRYING OUT THE INVENTION $R^1$, $R^2$, $R^3$, $R^4$, $R^5$, $R^6$, $R^7$, $R^8$ and A in the formula (I) will be described in detail below.

The alkyl or alkyl moiety in each of $R^1$, $R^2$, $R^3$, $R^4$, $R^5$, $R^6$, $R^7$, $R^8$ and A may be linear or branched, and specific examples thereof include $C_{1-9}$ alkyl such as methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl and n-nonyl.

Examples of the cycloalkyl or cycloalkyl moiety in each of $R^1$ and $R^5$ include $C_{3-6}$ cycloalkyl such as cyclopropyl, cyclobutyl, cyclopentyl and cyclohexyl.

The alkenyl or alkenyl moiety in each of $R^5$ and $R^7$ may be linear or branched, and specific examples thereof include $C_{2-9}$ alkenyl such as vinyl, 1-propenyl, 2-propenyl, isopropenyl, allyl, 1-butenyl, 2-butenyl, 3-butenyl, 1,3-butadienyl, 2-pentenyl, 4-pentenyl, 2-hexenyl, 4-hexenyl, 2-heptenyl, 4-heptenyl, 2-octenyl, 6-octenyl and 2-nonenyl.

The alkynyl or alkynyl moiety in each of $R^5$ and $R^7$ may be linear or branched, and specific examples thereof include $C_{2-9}$ alkynyl such as ethynyl, propargyl, 1-propynyl, 1-pentynyl, 3-pentynyl, 1-heptynyl and 1-nonynyl.

Examples of halogen or halogen as the substituent in each of $R^4$, $R^5$, $R^6$, $R^7$ and $R^8$ include atoms of fluorine, chlorine, bromine and iodine.

The number of halogens as substituents in each of $R^4$, $R^5$, $R^6$ and $R^7$ may be 1 or more, and if more, they may be the same or different. Further, the positions for substitution of such halogens may be any positions.

The number of alkoxy or alkoxy moieties as substituents in each of $R^5$ and $R^7$ may be 1 or more, and if more, they may be the same or different. Further, the positions for substitution may be any positions.

Examples of the aryl moiety as the substituent in $R^7$ include phenyl and naphthyl. The number of aryl or aryl moieties as substituents may be 1 or more, and if more, they may be the same or different. Further, the positions for substitution may be any positions.

The number of $R^8$ as substituents which substitute the arylalkyl in $R^7$ may be 1 or more, and if more, they may be the same or different. Further, the positions for substitution of such substituents may be any positions.

The alkoxyalkoxy in $R^5$ is meant for an alkoxy group having the same or different alkoxy moiety bonded thereto. The position for substitution of the alkoxy moiety which substitutes the alkoxy group may be any position. The same applies to haloalkoxyalkoxy, alkoxyhaloalkoxy, alkoxyalkoxyalkyl, alkylthioalkylthio, alkylsulfonylalkyl, alkoxycarbonylalkyl, etc.

The heterocyclyl moiety in $R^5$ may, for example, be a saturated or unsaturated 5-membered or 6-membered ring containing 1 to 4 one or more types of hetero atoms optionally selected from O, S and N, and specific examples thereof include oxolanyl, 1,3-dioxolanyl, tetrahydrofuranyl and tetrahydro-2H-pyranyl. Further, the number of heterocyclyl moieties as substituents may be 1 or more, and if more, they may be the same or different. The positions for substitution of the heterocyclyl moieties may be any positions.

The alkylene moiety in A may, for example, be $C_{1-9}$ alkylene such as methylene, ethylene, trimethylene, tetramethylene, pentamethylene, hexamethylene, heptamethylene, octamethylene or nonamethylene.

The salt of the herbicidal benzoylpyrazole compound of the formula (I) includes all kinds of salts so long as they are agriculturally acceptable. Examples thereof include alkali metal salts such as a sodium salt and a potassium salt; alkaline earth metal salts such as a magnesium salt and a calcium salt; amine salts such as a dimethylamine salt and a triethylamine salt; inorganic acid salts such as a hydrochloride, a perchlorate, a sulfate and a nitrate; and organic acid salts such as an acetate and a methanesulfonate.

In a case where various structural isomers such as optical isomers, geometric isomers, etc. exist as the compound Q, they are, of course, all included.

Other herbicidal compound in the present invention includes, for example, the following compounds (by common names including ones under application for approval by ISO, or test codes), and one or more may suitably be selected. Even when not specifically mentioned here, in a case where such compounds have salts, alkyl esters, hydrates, different crystal forms, various structural isomers, etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol or chlorflurenol-methyl.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton or trietazine; a triazine type such as simazine, atrazine, atratone, simetryn, prometryn, dimethametryn, hexazinone, metribuzin, terbuthylazine, cyanazine, ametryn, cybutryne, triaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl or bencarbazone.

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione (AVH-301), isoxaflutole, difenzoquat, difenzoquat-metilsulfate, isoxachlortole, benzobicyclon, picolinafen or beflubutamid.

(6) Those which exhibit strong herbicidal effects specifically to gramineous plants, such as an aryloxyphenoxypropionic acid type such as diclofop-methyl, diclofop, pyriphenopsodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, flazasulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron (TH-547) or a compound disclosed in the claim of WO2005092104; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium or propoxycarbazone; and others such as glyphosate, glyphosate sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chiorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochloror dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, pinoxaden, ipfencarbazone (HOK-201), aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras*.

The herbicidal composition of the present invention has excellent herbicidal effects. The application range extends to agricultural fields such as paddy fields, crop plant fields, orchards and mulberry fields and non-agricultural fields such as forest land, farm roads, play grounds and factory sites. The application method may suitably be selected from soil application, foliar application, water application, etc.

The herbicidal composition of the present invention are capable of controlling a wide range of undesired weeds, such as gramineae such as bamyardgrass (*Echinochloa crus-galli* L., *Echinochloa oryzicola* vasing.), crabgrass (*Digitaria sanguinalis* L., *Digitaria ischaemum* Muhl., *Digitaria adscendens* Henr., *Digitaria microbachne* Henr., *Digitaria horizontalis* Willd.), green foxtail (*Setaria viridis* L.), giant foxtail (*Setaria faberi* Herrm.), yellow foxtail (*Setaria lutescens* Hubb.), goosegrass (*Eleusine indica* L.), wild oat (*Avena fatua* L.), johnsongrass (*Sorghum halepense* L.), quackgrass (*Agropyron repens* L.), alexandergrass (*Brachiaria plantaginea*), guineagrass (*Panicum maximum* Jacq.), paragrass (*Panicum purpurascens*), sprangletop (*Leptochloa chinensis*), red sprangletop (*Leptochloa panicea*), annual bluegrass (*Poe annua* L.), black grass (*Alopecurus mvosuroides* Huds.), cholorado bluestem (*Agropvron tsukushiense* (Honda) Ohwi), broadleaf signalgrass (*Brachiaria platvphylla* Nash), southern sandbur (*Cenchrus echinatus* L.), italian ryegrass (*Lolium multiflorum* Lam.), and bermudagrass (*Cynodon dactylon* Pers.); cyperaceae such as rice flatsedge (*Cyperus iria* L.), purple nutsedge (*Cyperus rotundus* L.), yellow nutsedge (*Cvperus esculentus* L.), Japanese bulrush (*Scirpus juncoides*), flatsedge (*Cyperus serotinus*), small-flower umbrellaplant (*Cyperus difformis*), slender spikerush (*Eleocharis acicularis*), and water chestnut (*Eleocharis kuroquwai*); alismataceae such as Japanese ribbon waparo (*Sagittaria pygmaea*), arrow-head (*Sagittaria trifolia*), and narrowleaf waterplantain (*Alisma canaliculatum*); pontederiaceae such as monochoria (*Monochoria vaginalis*), and monochoria species (*Monochoria korsakowii*); scrophulariaceae such as false pimpernel (*Lindemia pvxidaria*), and abunome (*Dopatrium junceum*); lythraceae such as toothcup (*Rotala india*), and red stem (*Ammannia multiflora*); elatinaceae such as long stem waterwort (*Elatine triandra* SCHK.); malvaceae such as velvetleaf (*Abutilon theophrasti* MEDIC.), and prickly sida (*Side spinosa* L.); compositae such as common cocklebur (*Xanthium strumarium* L.), common ragweed (*Ambrosia elatior* L.), thistle (*Breea setosa* (BIEB.) KITAM.), hairy galinsoga (*Galinsoga ciliata* Blake), wild chamomile (*Matricaria chamomilla* L.); solanaceae such as black nightshade (*Solanum nigrum* L.), and jimsonweed (*Datura stramonium*); amaranthaceae such as slender amaranth (*Amaranthus viridis* L.), and redroot pigweed (*Amaranthus retroflexus* L.); polygonaceeae such as pale smartweed (*Polygonum lapathifolium* L.), ladysthumb (*Polygonum persicaria* L.), wild buckwheat (*Polygonum convolvulus* L.), and knotweed (*Polygonum aviculare* L.); cruciferae such as flexuous bittercress (*Cardamine flexuosa* WITH.), shepherd's-purse (*Capsella bursa-pastoris* Medik.), and indian mustard (*Brassica juncea* Czern.); convolvulaceae such as tall morningglory (*Ipomoea purpurea* L.), field bindweed (*Calystegia arvensis* L.), and ivyleaf morningglory (*Ipomoea hederacea* Jacq.); Chenopodiaceae such as common lambsquarters (*Chenopodium album* L.), and mexican burningbush (*Kochia scoparia* Schrad.); Portulacaceae such as common purslane (*Portulaca oleracea* L.); leguminosae such as sicklepod (*Cassia obtusifolia* L.); caryophyllaceae such as common chickweed (*Stellaria media* L.); labiatae such as henbit (*Lamium amplexicaule* L.); rubiaceae such as catchweed (*Galium spurium* L.); euphorbiaceae such as threeseeded copperleaf (*Acalvpha australis* L.); and Commelinaceae such as common dayflower (*Commelina communis* L.).

Therefore, they can be effectively used for selectively controlling noxious weeds in cultivation of useful crops such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), rye (*Secale cereale* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawngrass (*Zoysia japonica stend*), peanut (*Arachis hypogaea* L.), flax (*Linum usitatissimum* L.), tobacco (*Nicotiana tabacum* L.), and coffee (*Coffea* spp.). Particularly, the herbicidal composition of the present invention are effectively used for selectively controlling noxious weeds in cultivation of corn, soybean, cotton, wheat, rice, rape, sunflower, sugar beet, sugar cane, japanese lawngrass, peanut, flax, tobacco, coffee, and the like, and among these, especially corn, wheat, rice, and the like. And the herbicidal composition of the present invention can be effectively used for nonselectively controlling noxious weeds.

The herbicidal composition of the present invention is effectively used to selectively control noxious weeds in cultivation of various transformed plants. Examples of the transformed plants include pest-resistant transformed plants, phytopathogen-resistant transformed plants, transformed plants regarding plant components, transformed plants resistant to the compound Q, and transformed plants resistant to other herbicidal compound.

Examples of a site where the herbicidal composition of the present invention is applied include a corn field, a wheat, a barley or a rye field, a rice field and a non-agricultural field. One or more of other herbicidal compounds may suitably be selected and used depending upon the application site, and examples thereof include the following.

In a case where undesired plants are selectively controlled in a corn field, for example, said other herbicidal compound is at least one compound selected from the group consisting of a phenoxy compound, an aromatic carboxylic acid compound, a urea compound, a triazine compound, a hydroxybenzonitrile compound, a diphenylether compound, a cyclic imide compound, a pyrazole compound, a sulfonylurea compound, a triazolopyrimidinesulfonamide compound, an imidazolinone compound, a dinitroaniline compound, a chloroacetamide compound, a thiocarbamate compound, benazolin, benazolin-ethyl, diflufenzopyr, diflufenzopyr-sodium, fluoroxypyr, fluoroxypyr-2-butoxy-1-methylethyl, fluoroxypyr-meptyl, pyridate, bentazone, bentazone-sodium, amicarbazone, carfentrazone-ethyl, saflufenacil, flufenpyr-ethyl, bencarbazone, fluridone, clomazone, sulcotrione, mesotrione, tembotrione, isoxaflutole, difenzoquat, difenzoquat-metilsulfate, isoxachlortole, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, flufenacet, tridiphane, benfuresate, pyroxasulfone, dalapon, dalapon-sodium, dinoterb, dinoterb-ammonium, dinoterb-diolamine, dinoterb-acetate and DNOC.

More preferably, a phenoxy compound such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl or mecoprop-P-potassium; an aromatic carboxylic acid compound such as dicamba, dicamba-butotyl, dicamba-diglycolamine, dicamba-dimethylammonium, dicamba-diolamine, dicamba-isopropylammonium, dicamba-potassium, dicamba-sodium, clopyralid, clopyralid-olamine, clopyralid-potassium or clopyralid-triisopropanolammonium; a urea compound such as diuron, linuron, metobenzuron, methabenzthiazuron or monolinuron; a triazine compound such as simazine, atrazine, metribuzin, terbuthylazine, cyanazine, ametryn, terbutryn or propazine; a hydroxybenzonitrile compound such as bromoxynil, bromoxynil-octanoate or bromoxynil-heptanoate; a diphenylether compound such as bifenox, oxyfluorfen or aclonifen; a cyclic imide compound such as flumiclorac-pentyl, cinidon-ethyl or fluthiacet-methyl; a pyrazole compound such as topramezone; a sulfonylurea compound such as primisulfuron-methyl, primisulfuron, rimsulfuron, nicosulfuron, prosulfuron, flupyrsulfuron-methyl-sodium, flupyrsulfuron, halosulfuron-methyl, halosulfuron, thifensulfuron-methyl, thifensulfuron, iodosulfuron, iodosulfuron-methyl-sodium, tritosulfuron or foramsulfuron; a triazolopyrimidinesulfonamide compound such as flumetsulam, metosulam or florasulam: an imidazolinone compound such as imazamox or imazamox-ammonium; a dinitroaniline compound such as pendimethalin, ethalfluralin or prodiamine; a chloroacetamide compound such as alachlor, metazachior, metolachlor, S-metolachlor, pethoxamid, acetochlor, propachior, dimethenamid or dimethenamid-P; a thiocarbamate compound such as EPTC, butyrate, triallate or orbencarb; benazolin; benazolin-ethyl; diflufenzopyr, diflufenzopyr-sodium; fluoroxypyr; fluoroxypyr-2-butoxy-1-methylethyl; fluoroxypyr-meptyl; pyridate; bentazone; bentazone-sodium; amicarbazone; carfentrazone-ethyl; saflufenacil; flufenpyr-ethyl; bencarbazone; fluridone; clomazone; sulcotrione; mesotrione; tembotrione; isoxaflutole; difenzoquat; difenzoquat-metilsulfate; isoxachlortosinate-ammonium; flufenacet; tridiphane; benfuresate; pyroxasulfone; dalapon, dalapon-sodium; dinoterb; dinoterb-ammonium; dinoterb-diolamine, dinoterb-acetate; or DNOC may, for example, be used.

In a case where undesired plants are selectively controlled in a wheat, a barley or a rye field, for example, said other herbicidal compound is at least one compound selected from the group consisting of a phenoxy compound, an aromatic carboxylic acid compound, a urea compound, a triazine compound, an anilide compound, a hydroxybenzonitrile compound, a diphenylether compound, a cyclic imide compound, a pyrazole compound, an aryloxyphenoxypropionic acid compound, a cyclohexanedione compound, a sulfonylurea compound, a triazolopyrimidinesulfonamide compound, an imidazolinone compound, a pyrimidinylsalicylic acid compound, a sulfonylaminocarbonyltriazolinone compound, a dinitroaniline compound, a phenyl carbamate compound, a chloroacetamide compound, a thiocarbamate compound, benazolin, benazolin-ethyl, quinclorac, quinmerac, fluoroxypyr, fluoroxypyr-2-butoxy-1-methylethyl, fluoroxypyr pyridate, bentazone, bentazone-sodium, carfentrazone-ethyl, thidiazimin, pyraflufen-ethyl, saflufenacil, flupoxam, fluazolate, bencarbazone, flurtamone, diflufenican, sulcotrione, difenzoquat, difenzoquat-metilsulfate, picolinafen, beflubutamid, flamprop-M-methyl, flamprop-M, flamprop-M¬ isopropyl, flufenacet, indanofan, pinoxaden, dinoterb, dinoterb-ammonium, dinoterb-diolamine, dinoterb-acetate, DNOC and isoxaben.

More preferably, a phenoxy compound such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl or mecoprop-P-potassium; an aromatic carboxylic acid compound such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, clopyralid, clopyralid-olamine, clopyralid-potassium, clopyralid-triisopropanolammonium or aminopyralid; a urea compound such as chlorotoluron, diuron, linuron, isoproturon, dimefuron, methabenzthiazuron, metoxuron or neburon; a triazine compound such as prometryn, metribuzin, cyanazine or terbutryn; an anilide compound such as propanil or cypromid, a hydroxybenzonitrile compound such as bromoxynil, bromoxynil-octanoate, bromoxynil-heptanoate, ioxynil, ioxynil-octanoate, ioxynil-potassium or ioxynil-sodium; a diphenylether compound such as bifenox, oxyfluorfen, aclonifen, ethoxyfen-ethyl, fluoroglycofen-ethyl or fluoroglycofen; a cyclic imide compound such as cinidon-ethyl, a pyrazole compound such as pyrasulfotole; an aryloxyphenoxypropionic acid compound such as diclofop-methyl, diclofop, fenoxaprop-ethyl, fenoxaprop-P, fenoxaprop-P-ethyl, clodinafop-propargyl or clodinafop; a cyclohexanedione compound such as tralkoxydim or butroxydim; a sulfonylurea compound such as chiorsulfuron, metsulfuron-methyl, metsulfuron, cyclosulfamuron, prosulfuron, flupyrsulfuron-methyl-sodium, flupyrsulfuron, halosulfuron-methyl, halosulfuron, thifensulfuron-methyl, thifensulfuron, ethoxysulfuron, iodosulfuron-methyl-sodium, iodosulfuron, sulfosulfuron, triasulfuron, tribenuron methyl, tribenuron, tritosulfuron, mesosulfuron-methyl, mesosulfuron, flucetosulfuron or amidosulfuron; a triazolopyrimidinesulfonamide compound such as flumetsulam, metosulam or florasulam; an imidazolinone compound such as imazamox, imazamox-ammonium, imazamethabenz or imazamethabenz-methyl; a pyrimidinylsalicylic acid compound such as pyribenzoxim; a sulfonylaminocarbonyltriazolinone compound such as flucarbazone, flucarbazone sodium, propoxycarbazone or propoxycarbazone-sodium; a dinitroaniline compound such as pendimethalin or butralin; a phenyl carbamate compound such as barban; a chloroacetamide compound such as butachlor; a thiocarbamate compound such as prosulfocarb, triallate or orbencarb; benazolin, benazolin-ethyl, quinclorac, quinmerac, fluoroxypyr, fluoroxypyr-2-butoxy-1-methylethyl, fluoroxypyr-meptyl, pyridate, bentazone, bentazone-sodium, carfentrazone-ethyl, thidiazimin, pyraflufen-ethyl, saflufenacil, flupoxam, fluazolate, bencarbazone, flurtamone, diflufenican, sulcotrione, difenzoquat, difenzoquat-metilsulfate, picolinafen, beflubutamid, flamprop-M-methyl, flamprop-M, flamprop-M-isopropyl, flufenacet, indanofan, pinoxaden, dinoterb, dinoterb-ammonium, dinoterb-diolamine, dinoterb-acetate, DNOC; or isoxaben may, for example, be used.

In a case where undesired plants are selectively controlled in a rice field, for example, said other herbicidal compound is at least one compound selected from the group consisting of a phenoxy compound, an aromatic carboxylic acid compound, a urea compound, a triazine compound, an anilide compound, a carbamate compound, a diphenylether compound, a pyrazole compound, an aryloxyphenoxypropionic acid compound, a cyclohexanedione compound, a sulfonylurea compound, a triazolopyrimidinesulfonamide compound, a pyrimidinylsalicylic acid compound, a dinitroaniline compound, an organic phosphorus compound, a cumylamine compound, a chloroacetamide compound, a thiocarbamate compound, those which are believed to exhibit herbicidal effects by being parasitic on plants, quinclorac, quinmerac, pyridate, bentazone, bentazone-sodium, oxadiargyl, oxadiazon, carfentrazone-ethyl, pentoxazone, pyraclonil, fluridone, diflufenican, methoxyphenone, clomazone, mesotrione, tefuryltrione, benzobicyclon, cinmethylin, dithiopyr, etobenzanide, mefenacet, flufenacet, cafenstrole, fentrazamide, oxaziclomefone, indanofan, benfuresate, TCA-sodium, trichloroacetic acid, ipfencarbazone and quinoclamine.

More preferably, a phenoxy compound such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid compound such as picloram, picloram-dimethylammonium, picloram-isoctyl, picloram-potassium, picloram-triisopropanolammonium, picloram-triisopropylammonium, picloram-trolamine, triclopyr, triclopyr-butotyl or triclopyr-triethylammonium; a urea compound such as linuron; a triazine compound such simetryn, prometryn, dimethametryn or triaziflam; an anilide compound such as propanil; a carbamate compound such as swep; a diphenylether compound such as nitrofen, chlomethoxyfen, bifenox, acifluorfen, acifluorfen-sodium, oxyfluorfen, fluoroglycofen-ethyl or fluoroglycofen; a pyrazole compound such as pyrazolynate, pyrazoxyfen or benzofenap; an aryloxyphenoxypropionic acid compound such as cyhalofop-butyl, metamifop-propyl or metamifop; a cyclohexanedione compound such as profoxydim; a sulfonylurea compound such as bensulfuron-methyl, bensulfuron, metsulfuron-methyl, metsulfuron, cinosulfuron, pyrazosulfuron-ethyl, pyrazosulfuron, azimsulfuron, imazosulfuron, cyclosulfamuron, halosulfuron-methyl, halosulfuron, ethoxysulfuron, orthosulfamuron, flucetosulfuron or propyrisulfuron; a triazolopyrimidinesulfonamide compound such as penoxsulam; a pyrimidinylsalicylic acid compound such as bispyribac-sodium, pyriminobac-methyl, pyribenzoxim, pyriftalid or pyrimisulfan; a dinitroaniline compound such as oryzalin, pendimethalin or butralin; an organic phosphorus compound such as butamifos, anilofos or piperophos; a cumylamine compound such as daimuron, cumyluron or bromobutide; a chloroacetamide compound such as butachlor, pretilachloror thenylchlor; a thiocarbamate compound such as molinate, dimepiperate, pyributicarb, esprocarb or thiobencarb; quinclorac; quinmerac; pyridate; bentazone; bentazone-sodium; oxadiargyl; oxadiazon; carfentrazone-ethyl; pentoxazone; pyraclonil, fluridone; diflufenican; methoxyphenone; clomazone; mesotrione; tefuryltrione; benzobicyclon; cinmethylin; dithiopyr; etobenzanide; mefenacet; flufenacet; cafenstrole; fentrazamide; oxaziclomefone; indanofan; benfuresate; TCA-sodium; trichloroacetic acid; ipfencarbazone; or quinoclamine may, for example, be used.

In a case where undesired plants are nonselectively controlled, for example, said other herbicidal compound is at least one compound selected from the group consisting of a phenoxy compound, an aromatic carboxylic acid compound, a urea compound, a triazine compound, a uracil compound, a hydroxybenzonitrile compound, a quaternary ammonium salt compound, a sulfonylurea compound, an imidazolinone compound, a pyrimidinylsalicylic acid compound, a dinitroaniline compound, benazolin, benazolin-ethyl, diflufenzopyr, diflufenzopyr-sodium, chlorflurenol, chlorflurenol-methyl, pentanochior, butafenacil, glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium, asulam, asulam-sodium, dalapon, dalapon-sodium, TCA-sodium, trichloroacetic acid, CMA, fosamine, fosamine-ammonium, ammonium sulfamate, borax, chloroacetic acid, sodium chloroacete, methylarsonic acid, dimethylarsinic acid, sodium dimethylarsinate, flupropanate, flupropanate-sodium, isoxaben, mefluidide, mefluidide-diolamine, pentachlorophenol, pentachlorophenol-sodium and pentachlorophenol-laurate.

More preferably, a phenoxy compound such as 2,4-D, 2,4-D-butotyl, 2,4-D-butyl, 2,4-D-dimethylammonimum, 2,4-D-diolamine, 2,4-D-ethyl, 2,4-D-2-ethylhexyl, 2,4-D-isobutyl, 2,4-D¬ isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichiorprop, dichlorprop-butotyl, dichlorprop-dimethylammonium, dichlorprop-isoctyl, dichiorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl or mecoprop-P-potassium; an aromatic carboxylic acid compound such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; a urea compound such as diuron, tebuthiuron, isouron, karbutilate, monolinuron or neburon; a triazine compound such as atrazine, hexazinone, terbuthylazine, cyanazine, ametryn, propazine or prometon; a uracil compound such as bromacil or bromacyl-lithium; a hydroxybenzonitrile compound such as bromoxynil, bromoxynil-octanoate or bromoxynil-heptanoate; a quaternary ammonium salt compound such as paraquat or diquat; a sulfonylurea compound such as sulfometuron-methyl, sulfometuron, chlorsulfuron, flazasulfuron or sulfosulfuron; an imidazolinone compound such as imazapyr, imazapyr-isopropylammonium or imazapic; a pyrimidinylsalicylic acid compound such as bispyribac-sodium; a dinitroaniline compound such as oryzalin or prodiamine; benazolin; benazolin-ethyl; diflufenzopyr; diflufenzopyr-sodium; chlorfiurenol; chlorfiurenol-methyl; pentanochior; butafenacil; glyphosate; glyphosate-sodium; glyphosate-potassium; glyphosate-ammonium; glyphosate-diammonium; glyphosate-isopropylammonium; glyphosate-trimesium; glyphosate-sesquisodium; glufosinate; glufosinate-ammonium; glufosinate-P, glufosinate-P-ammonium, glufosinate-P-sodium, bilanafos; bilanafos-sodium; asulam; asulam-sodium; dalapon; dalapon-sodium; TCA-sodium; trichloroacetic acid; CMA; fosamine; fosamine-ammonium; ammonium sulfamate; borax; chloroacetic acid; sodium chloroacete; methylarsonic acid; dimethylarsinic acid; sodium dimethylarsinate; flupropanate; flupropanate-sodium; isoxaben; mefluidide; mefluidide-diolamine; pentachlorophenol; sodium pentachlorophenoxide or pentachlorophenol laurate may, for example, be used.

In the present invention, the mixing ratio of the compound Q to said other herbicidal compound cannot generally be defined, as it varies depending upon various conditions such as the type of the compound, the type of the formulation, the weather conditions, and the type and the growth state of the plants to be controlled, but it is usually from 1:2,000 to 1,000:1, preferably from 1:1,500 to 100:1, more preferably from 1:1,200 to 30:1 by the weight ratio.

Said other herbicidal compound in the present invention is not particularly limited to a specific compound, and the mixing ratio with the compound Q is not limited to a specific range, but as one embodiment of the present invention, mixing ratios of the compound Q to some compounds are exemplified. However, the ratio may also vary depending upon various conditions such as the type of the compound, the type of formulation, the weather conditions, and the type and the growth state of the plants to be controlled as described above.

In a case where said other herbicidal compound is a phenoxy compound, the mixing ratio of (a) the compound Q to (b) the phenoxy compound is usually from 1:1 to 1:500, preferably from 1:1 to 1:100, more preferably from 1:5 to 1:50 by the weight ratio. In a case where said other herbicidal compound is an aromatic carboxylic acid compound, the mixing ratio of (a) the compound Q to (b) the aromatic carboxylic acid compound is usually from 1:1 to 1:500, preferably from 1:1 to 1:100, more preferably from 1:5 to 1:70 by the weight ratio.

In a case where said other herbicidal compound is fluoroxypyr, the mixing ratio of (a) the compound Q to (b) fluoroxypyr is usually from 1:1: to 1:500, preferably from 1:1 to 1:100, more preferably from 1:5 to 1:50 by the weight ratio.

In a case where said other herbicidal compound is a triazine compound, the mixing ratio of (a) the compound Q to (b) the triazine compound is usually from 1:2,000 to 1,000:1, preferably from 1:1,500 to 10:1, more preferably from 1:1,200 to 5:1 by the weight ratio.

In a case where said other herbicidal compound is a urea compound, the mixing ratio of (a) the compound Q to (b) the urea compound is usually from 1:1 to 1:500, preferably from 1:5 to 1:200, more preferably from 1:20 to 1:60 by the weight ratio.

In a case where said other herbicidal compound is a hydroxybenzonitrile compound, the mixing ratio of (a) the compound Q to (b) the hydroxybenzonitrile compound is usually from 1:500 to 50:1, preferably from 1:100 to 20:1, more preferably from 1:40 to 6:1 by the weight ratio. In a case where said other herbicidal compound is bentazone or its salt (such as bentazone-sodium), the mixing ratio of (a) the compound Q to (b) bentazone or its salt is usually from 1:1 to 1:500, preferably from 1:1 to 1:100, more preferably from 1:1 to 1:40 by the weight ratio.

In a case where said other herbicidal compound is a diphenylether compound, the mixing ratio of (a) the compound Q to (b) the diphenylether compound is usually from 1:1 to 1:500, preferably from 1:1 to 1:100, more preferably from 1:5 to 1:30 by the weight ratio.

In a case where said other herbicidal compound is a cyclic imide compound, the mixing ratio of (a) the compound Q to (b) the cyclic imide compound is usually from 1:50 to 100:1, preferably from 1:50 to 50:1, more preferably from 1:10 to 20:1 by the weight ratio.

In a case where said other herbicidal compound is carfentrazone-ethyl, the mixing ratio of (a) the compound Q to (b) carfentrazone-ethyl is usually from 1:100 to 100:1, preferably from 1:20 to 10:1, more preferably from 1:10 to 10:1 by the weight ratio.

In a case where said other herbicidal compound is pyridate, the mixing ratio of (a) the compound Q to (b) pyridate is usually from 1:1 to 1:500, preferably from 1:1 to 1:100, more preferably from 1:10 to 1:40 by the weight ratio. In a case where said other herbicidal compound is sulcotrione, the mixing ratio of (a) the compound 0 to (b) sulcotrione is usually from 1:100 to 10:1, preferably from 1:10 to 10:1, more preferably from 1:5 to 2:1 by the weight ratio.

In a case where said other herbicidal compound is mesotrione, the mixing ratio of (a) the compound Q to (b) mesotrione is usually from 1:1 to 1:100, preferably from 1:1 to 1:50, more preferably from 1:1 to 1:10 by the weight ratio.

In a case where said other herbicidal compound is a sulfonylurea compound, the mixing ratio of (a) the compound Q to (b) the sulfonylurea compound is usually from 1:100 to 100:1, preferably from 1:70 to 50:1, more preferably from 1:50 to 30:1 by the weight ratio.

In a case where said other herbicidal compound is a triazolopyrimidinesulfonamide compound, the mixing ratio of (a) the compound Q to (b) the triazolopyrimidinesulfonamide compound is usually from 1:100 to 100:1, preferably from 1:50 to 10:1, more preferably from 1:10 to 5:1 by the weight ratio.

In a case where said other herbicidal compound is an imidazolinone compound, the mixing ratio of (a) the compound Q to (b) the imidazolinone compound is usually from 1:100 to 100:1, preferably from 1:50 to 10:1, more preferably from 1:10 to 5:1 by the weight ratio.

In a case where said other herbicidal compound is glyphosate or its salt (such as glyphosate-ammonium), the mixing ratio of (a) the compound Q to (b) glyphosate or its salt is usually from 1:1 to 1:500, preferably from 1:1 to 1:100, more preferably from 1:1 to 1:80 by the weight ratio.

In a case where said other herbicidal compound is glufosinate, glufosinate-P or its salt (such as glufosinate-ammonium, glufosinate-P-ammonium), the mixing ratio of (a) the compound Q to (b) glufosinate, glufosinate-P or its salt is usually from 1:1 to 1:500, preferably from 1:1 to 1:100, more preferably from 1:1 to 1:40 by the weight ratio.

In a case where said other herbicidal compound is a dinitrianiline compound, the mixing ratio of (a) the compound Q to (b) the dinitrianiline compound is usually from 1:1 to 1:1,000, preferably from 1:1 to 1:100, more preferably from 1:1 to 1:50 by the weight ratio.

In a case where said other herbicidal compound is a chloroacetamide compound, the mixing ratio of (a) the compound Q to (b) the chloroacetamide compound is usually from 1:1 to 1:1,000, preferably from 1:1 to 1:500, more preferably from 1:1 to 1:300 by the weight ratio.

In a case where said other herbicidal compound is flufenacet, the mixing ratio of (a) the compound Q to (b) flufenacet is usually from 1:1 to 1:500, preferably from 1:5 to 1:100, more preferably from 1:15 to 1:50 by the weight ratio.

In a case where said other herbicidal compound is pyroxasulfone, the mixing ratio of (a) the compound Q to (b) pyroxasulfone is usually from 1:1 to 1:500, preferably from 1:1 to 1:100, more preferably from 1:1 to 1:50 by the weight ratio.

The dose of the herbicidally active ingredients in the present invention cannot generally be defined, as it varies depending upon various conditions such as the types of the compound Q and other herbicidal compound, their mixing ratio, the type of the formulation, the weather conditions, and the type and the growth state of the plants to be controlled. However, the compound Q is applied in an amount of usually from 0.1 to 10,000 g/ha, preferably from 1 to 2,000 g/ha, more preferably from 1 to 1,000 g/ha, and said other herbicidal compound is applied in an amount of usually from 0.1 to 50,000 g/ha, preferably from 1 to 10,000 g/ha, more preferably from 1.5 to 10,000 g/ha, and the appropriate dose of the compound Q and said other herbicidal compound in total is usually from 0.2 to 60,000 g/ha, preferably from 2 to 12,000 g/ha, more preferably from 2.5 to 11,000 g/ha.

Said other herbicidal compound in the present invention is not limited to a specific compound, and its dose is not limited to a specific range, but as one embodiment of the present invention, doses of some compounds are exemplified. However, the dose may vary depending upon various conditions such as the type of the compound, the type of the formulation, the weather conditions, and the type and the growth state of the plants to be controlled in some cases as described above.

In a case where other herbicidal compound is a phenoxy compound, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is an aromatic carboxylic acid compound, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is fluoroxypyr, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is a triazine compound, the dose of said other herbicidal compound is usually from 0.1 to 50,000 g/ha, preferably from 10 to 10,000 g/ha. Further, the appropriate dose of the compound Q and said other herbicidal compound in total is usually from 0.2 to 60,000 g/ha, preferably from 11 to 12,000 g/ha.

In a case where other herbicidal compound is a urea compound, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is a hydroxybenzonitrile compound, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is bentazone or its salt (such as bentazone-sodium), the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is a diphenylether compound, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is a cyclic imide compound, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is carfentrazone-ethyl, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is pyridate, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is sulcotrione, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is mesotrione, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is a sulfonylurea compound, the dose of said other herbicidal compound is usually from 0.1 to 10,000 g/ha, preferably from 1 to 500 g/ha. Further, the appropriate dose of the compound Q and said other herbicidal compound in total is usually from 0.2 to 20,000 g/ha, preferably from 2 to 2,500 g/ha.

In a case where other herbicidal compound is a triazolopyrimidinesulfonamide compound, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is an imidazolinone compound, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is glyphosate or its salt (such as glyphosate-ammonium), the dose of said other herbicidal compound is usually from 0.1 to 50,000 g/ha, preferably from 1 to 5,000 g/ha. Further, the appropriate dose of the compound Q and said other herbicidal compound in total is usually from 0.2 to 60,000 g/ha, preferably from 2 to 7,000 g/ha.

In a case where other herbicidal compound is glufosinate, glufosinate-P or its salt (such as glufosinate-ammonium, glufosinate-P-ammonium), the dose of said other herbicidal compound is usually from 0.1 to 50,000 g/ha, preferably from 1 to 5,000 g/ha. Further, the appropriate dose of the compound Q and said other herbicidal compound in total is usually from 0.2 to 60,000 g/ha, preferably from 2 to 7,000 g/ha.

In a case where other herbicidal compound is a dinitroaniline compound, the dose of said other herbicidal compound is usually from 0.1 to 10,000 g/ha, preferably from 1 to 5,000 g/ha. Further, the appropriate dose of the compound Q and said other herbicidal compound in total is usually from 0.2 to 20,000 g/ha, preferably from 2 to 7,000 g/ha.

In a case where other herbicidal compound is a chloroacetamide compound, the dose of said other herbicidal compound is usually from 0.1 to 50,000 g/ha, preferably from 1 to 10,000 g/ha. Further, the appropriate dose of the compound Q and said other herbicidal compound in total is usually from 0.2 to 60,000 g/ha, preferably from 2 to 12,000 g/ha.

In a case where other herbicidal compound is flufenacet, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

In a case where other herbicidal compound is pyroxasulfone, the dose of said other herbicidal compound is usually from 0.1 to 10,000 g/ha, preferably from 1 to 2,000 g/ha. Further, the appropriate dose of the compound Q and said other herbicidal compound in total is usually from 0.2 to 20,000 g/ha, preferably from 2 to 4,000 g/ha.

With respect to application, application to undesired plants or application to a place where they grow (either before or after emerging of the plants) may optionally be selected. Further, the compound Q and other herbicidal compound may separately be formulated so that they are mixed for use at the time of application, or they may be formulated together. As examples of a specific application method, the following may be mentioned.

1. The compound Q and other herbicidal compound are formulated together, and the formulation is applied as it is.
2. The compound Q and other herbicidal compound are formulated together, the formulation is diluted to a predetermined concentration with e.g. water, and as the case requires, a spreader (such as a surfactant, a vegetable oil or a mineral oil) is added for application.
3. The compound Q and other herbicidal compound are separately formulated and applied as they are.
4. The compound Q and other herbicidal compound are separately formulated, and they are diluted to a predetermined concentration with e.g. water, and as the case requires, a spreader (such as a surfactant, a vegetable oil or a mineral oil) is added for application.
5. The compound Q and other herbicidal compound are separately formulated, and the formulations are mixed when diluted to a predetermined concentration with e.g. water, and as the case requires, a spreader (such as a surfactant, a vegetable oil or a mineral oil) is added for application.

The herbicidal composition of the present invention may be prepared by mixing the compound Q and other herbicidal compound, as active ingredients, with various agricultural additives in accordance with conventional formulation methods for agricultural chemicals, and applied in the form of various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, the compound Q and other herbicidal compound may be mixed together for the formulation, or they may be separately formulated.

The additives to be used for the formulation include, for example, a solid carrier such as diatomaceous earth, slaked lime, calcium carbonate, talc, white carbon, kaoline, bentonite, kaolinite, sericite, clay, sodium carbonate, sodium bicarbonate, mirabilite, zeolite or starch; a solvent such as water, toluene, xylene, solvent naphtha, dioxane, acetone, isophorone, methyl isobutyl ketone, chlorobenzene, cyclohexane, dimethylsulfoxide, dimethylformamide, dimethylacetamide, N-methyl-2-pyrrolidone or an alcohol; an anionic surfactant or spreader such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonate condensed with formaldehyde or an alkylnaphthalene sulfonate condensed with formaldehyde; a nonionic surfactant or spreader such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the compound Q or other herbicidal compound to such various additives may be from 0.1:99.9 to 95:5, preferably from 0.2:99.8 to 85:15.

The herbicidal composition of the present invention may be mixed with or may be used in combination with other agricultural chemicals, fertilizers or phytotoxicity-reducing agents, whereby synergistic effects or activities may sometimes be obtained. Such other agricultural chemicals include, for example, a fungicide, an antibiotic, a plant hormone and an insecticide.

Now, examples of preferred embodiments of the present invention will be given below, but it should be understood that the present invention is by no means restricted thereto.

(1) A herbicidal composition comprising as active ingredients (a) a herbicidal benzoylpyrazole compound of the formula (I) or its salt wherein $R^1$ is alkyl, $R^2$ is a hydrogen atom or alkyl, $R^3$ is alkyl, $R^4$ is alkyl or halogen, $R^5$ is alkoxyalkyl, haloalkoxyalkyl, alkoxy, haloalkoxy, alkoxyalkoxy or —C(O)OR$^7$, $R^6$ is alkylsulfonyl, A is alkylene substituted by at least one alkyl, and $R^7$ is alkyl, and (b) other herbicidal compound.

(2) A herbicidal composition comprising as active ingredients (a) a herbicidal benzoylpyrazole compound of the formula (I) or its salt wherein $R^1$ is alkyl, $R^2$ is a hydrogen atom, $R^3$ is alkyl, $R^4$ is alkyl, $R^5$ is alkoxyalkyl, alkoxy, alkoxyalkoxy or —C(O)OR$^7$, $R^6$ is alkylsulfonyl, A is alkylene substituted by at least one alkyl, and $R^7$ is alkyl, and (b) other herbicidal compound.

(3) A herbicidal composition comprising as active ingredients (a) a herbicidal benzoylpyrazole compound of the formula (I) or its salt wherein $R^1$ is alkyl, $R^2$ is a hydrogen atom, $R^3$ is alkyl, $R^4$ is alkyl, $R^5$ is alkoxyalkoxy, $R^6$ is alkylsulfonyl, and A is alkylene substituted by at least one alkyl, and (b) other herbicidal compound.

(4) A herbicidal composition comprising as active ingredients (a) a herbicidal benzoylpyrazole compound of the formula (I) or its salt wherein $R^1$ is —$CH_3$ or —$CH_2CH_3$, $R^2$ is —H, $R^3$ is —$CH_3$ or —$CH_2CH_3$, $R^4$ is —$CH_3$, $R^5$ is —$OCH_2CH_2OCH_3$, $R^6$ is —$SO_2CH_3$ and A is —CH($CH_3$)—, and (b) other herbicidal compound.

Now, typical examples of the compound Q will be given in Table 1, but the compound Q in the present invention is not limited thereto. These compounds can be prepared in accordance with various processes disclosed in e.g. WO2007/069771 or WO2008/065907. Further, the after-mentioned Compound No. 4 may be prepared in accordance with the following Preparation Example.

Preparation Example

Preparation of 1-(1-ethyl-4-(3-(2-methoxyethoxy)-2-methyl-4-(methylsulfonyl)benzoyl)-1H-pyrazol-5-yloxy)ethyl methyl carbonate (the following Compound No. 4)

5-Hydroxy-1-ethylpyrazol-4-yl3-(2-methoxyethoxy)-2-methyl-4-(methylsulfonyl)phenyl ketone (300 mg) was dissolved in 2-butanone (10 mL), and potassium carbonate (130 mg) and tetrabutylammonium bromide (15 mg) were added. After stirring at room temperature for 10 minutes, 1-chloroethyl methyl carbonate (purity: 85%, 270 mg) was added at room temperature, followed by heating and refluxing for 3 hours. After completion of the reaction, the reaction mixture was cooled to room temperature and poured into water and then extracted with ethyl acetate. The organic layer was washed with 1N hydrochloric acid and a saturated sodium chloride aqueous solution, followed by drying over anhydrous sodium sulfate. The solvent was distilled off under reduced pressure. The obtained residue was purified by column chromatography with n-hexane:ethyl acetate=1:1, to obtain the desired product (180 mg) as slightly yellow solid. The NMR spectrum data of this product are as follows.

$^1$H-NMR δppm (measuring instrument:JEOL-GSX (400 MHz), solvent:CDCl$_3$) 1.40 (3H, t, J=7.2 Hz), 1.77 (3H, d, J=5.2 Hz), 2.35 (3H, s), 2.94 (3H, s), 3.46 (3H, s), 3.71 (3H, s), 3.80 (2H, t, J=4.4 Hz), 4.05 (2H, m), 4.24 (2H, t, J=4.4 Hz), 6.78 (1H, q, J=5.2 Hz), 7.26 (1H, d, J=7.6 Hz), 7.28 (1H, s), 7.88 (1H, d, J=7.6 Hz).

In Table 1, No. represents a Compound No. Further, in Table 1, Me represents a methyl group, Et an ethyl group, n-Pr a n-propyl group, i-Pr an isopropyl group, n-Bu a n-butyl group, and t-Bu a tertiary butyl group. Further, the left-hand side of -A- is bonded to the pyrazole side, and the right-hand side of -A- is bonded to the carbonate side.

TABLE 1

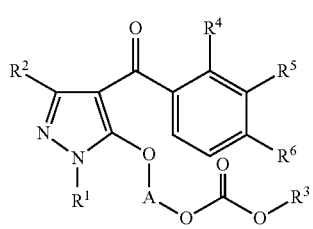

(I)

[HYO 1]

| No. | $R^1$ | $R^2$ | $R^3$ | $R^4$ | $R^5$ | $R^6$ | —A— |
|---|---|---|---|---|---|---|---|
| 1 | Me | H | Me | Me | OCH$_2$CH$_2$OMe | SO$_2$Me | —CH(Me)— |
| 2 | Me | H | Me | Me | OCH$_2$CH$_2$OMe | SO$_2$Me | —CH(Me)— |

TABLE 1-continued (I)

[Structure: pyrazole with R1 on N, R2 on C3, connected via C(=O) to phenyl ring bearing R4, R5, R6; pyrazole O-A-O-C(=O)-O-R3]

| No. | R¹ | R² | R³ | R⁴ | R⁵ | R⁶ | —A— |
|---|---|---|---|---|---|---|---|
| 3 | Et | H | Et | Me | OCH₂CH₂OMe | SO₂Me | —CH(Me)— |
| 4 | Et | H | Me | Me | OCH₂CH₂OMe | SO₂Me | —CH(Me)— |
| 5 | Me | H | Et | Me | OCH₂CH₂OMe | SO₂Me | —C(Me)₂— |
| 6 | Me | H | Et | Me | OCH₂CF₃ | SO₂Me | —CH(Me)— |
| 7 | Me | H | Et | Me | CH₂OMe | SO₂Me | —CH(Me)— |
| 8 | Me | H | Et | Cl | CH₂OMe | SO₂Me | —CH(Me)— |
| 9 | n-Bu | H | Et | Me | OCH₂CH₂OMe | SO₂Me | —CH(Me)— |
| 10 | t-Bu | H | Et | Me | OCH₂CH₂OMe | SO₂Me | —CH(Me)— |
| 11 | Me | Me | Et | Me | OCH₂CH₂OMe | SO₂Me | —CH(Me)— |
| 12 | Me | H | Et | Me | OCH₂CH₂OMe | SO₂Me | —C(Me)(Et)— |
| 13 | Me | H | Et | Me | OCH₂CH₂OMe | SO₂Me | —CH(Et)— |
| 14 | Me | H | Et | Me | OCH₂CH₂OMe | SO₂Me | —CH(i-Pr)— |
| 15 | Me | H | Et | Me | CH₂OCH₂CF₃ | SO₂Me | —CH(Me)— |
| 16 | Et | H | Et | Cl | C(O)OMe | SO₂Me | —CH(Me)— |
| 17 | Me | H | Et | Cl | OCH₂CH₂OMe | SO₂Me | —CH(Me)— |
| 18 | i-Pr | H | Et | Me | OCH₂CH₂OMe | SO₂Me | —CH(Me)— |
| 19 | Me | H | n-Pr | Me | OCH₂CH₂OMe | SO₂Me | —CH(Me)— |
| 20 | Me | H | n-Bu | Me | OCH₂CH₂OMe | SO₂Me | —CH(Me)— |
| 21 | Me | H | Et | Me | C(O)OMe | SO₂Me | —CH(Me)— |
| 22 | Me | H | Me | Me | OCH₂CH₂OMe | SO₂Me | —C(Me)₂— |
| 23 | Et | H | Et | Me | OCH₂CH₂OMe | SO₂Me | —C(Me)₂— |
| 24 | Me | H | i-Pr | Me | OCH₂CH₂OMe | SO₂Me | —C(Me)₂— |
| 25 | i-Pr | Me | Et | Me | OCH₂CH₂OMe | SO₂Me | —C(Me)₂— |
| 26 | Me | H | n-Pr | Me | OCH₂CH₂OMe | SO₂Me | —C(Me)₂— |
| 27 | Me | H | n-Bu | Me | OCH₂CH₂OMe | SO₂Me | —C(Me)₂— |
| 28 | Me | H | Et | Me | OCH₂CH₂OMe | SO₂Me | —C(Me)₂— |
| 29 | Et | H | Et | Cl | OCH₂CH₂OMe | SO₂Me | —CH(Me)— |

[HYO 2]

| No. | R¹ | R² | R³ | R⁴ | R⁵ | R⁶ | —A— |
|---|---|---|---|---|---|---|---|
| 30 | t-Bu | H | Et | Cl | OCH₂CH₂OMe | SO₂Me | —CH(Me)— |
| 31 | Me | Me | Et | Cl | OCH₂CH₂OMe | SO₂Me | —CH(Me)— |
| 32 | Me | H | Me | Me | OCH₂CH₂OMe | SO₂Et | —CH(Me)— |
| 33 | Me | H | Et | Me | OCH₂CH₂OMe | SO₂Et | —CH(Me)— |
| 34 | Et | H | Et | Me | OCH₂CH₂OMe | SO₂Et | —CH(Me)— |
| 35 | Me | H | i-Pr | Me | OCH₂CH₂OMe | SO₂Et | —CH(Me)— |
| 36 | Me | H | Et | Me | OCH₂CH₂OMe | SO₂Et | —C(Me)₂— |
| 37 | Me | H | Et | Me | OCH₂CF₃ | SO₂Et | —CH(Me)— |
| 38 | Me | H | Et | Me | CH₂OMe | SO₂Et | —CH(Me)— |
| 39 | Me | H | Et | Cl | CH₂OMe | SO₂Et | —CH(Me)— |
| 40 | n-Bu | H | Et | Me | OCH₂CH₂OMe | SO₂Et | —CH(Me)— |
| 41 | t-Bu | H | Et | Me | OCH₂CH₂OMe | SO₂Et | —CH(Me)— |
| 42 | Me | Me | Et | Me | OCH₂CH₂OMe | SO₂Et | —CH(Me)— |
| 43 | Me | H | Et | Me | OCH₂CH₂OMe | SO₂Et | —C(Me)(Et)— |
| 44 | Me | H | Et | Me | OCH₂CH₂OMe | SO₂Et | —CH(Et)— |
| 45 | Me | H | Et | Me | OCH₂CH₂OMe | SO₂Et | —CH(i-Pr)— |
| 46 | Me | H | Et | Me | CH₂OCH₂CF₃ | SO₂Et | —CH(Me)— |
| 47 | Et | H | Et | Cl | C(O)OMe | SO₂Et | —CH(Me)— |
| 48 | Me | H | Et | Cl | OCH₂CH₂OMe | SO₂Et | —CH(Me)— |
| 49 | i-Pr | Me | Et | Me | OCH₂CH₂OMe | SO₂Et | —CH(Me)— |
| 50 | Me | H | n-Pr | Me | OCH₂CH₂OMe | SO₂Et | —CH(Me)— |
| 51 | Me | H | n-Bu | Me | OCH₂CH₂OMe | SO₂Et | —CH(Me)— |
| 52 | Me | H | Et | Me | C(O)OMe | SO₂Et | —CH(Me)— |
| 53 | Me | H | Me | Me | OCH₂CH₂OMe | SO₂Et | —C(Me)₂— |
| 54 | Et | H | Et | Me | OCH₂CH₂OMe | SO₂Et | —C(Me)₂— |
| 55 | Me | H | i-Pr | Me | OCH₂CH₂OMe | SO₂Et | —C(Me)₂— |
| 56 | Me | H | Me | Br | OCH₂CH₂OMe | SO₂Me | —CH(Me)— |
| 57 | Me | H | Et | Br | OCH₂CH₂OMe | SO₂Me | —CH(Me)— |
| 58 | Et | H | Et | Br | OCH₂CH₂OMe | SO₂Me | —CH(Me)— |
| 59 | Me | H | i-Pr | Br | OCH₂CH₂OMe | SO₂Me | —CH(Me)— |
| 60 | Me | H | Et | Br | OCH₂CH₂OMe | SO₂Me | —C(Me)₂— |
| 61 | Me | H | Et | Br | OCH₂CF₃ | SO₂Me | —CH(Me)— |
| 62 | Me | H | Et | Br | CH₂OMe | SO₂Me | —CH(Me)— |
| 63 | n-Bu | H | Et | Me | OCH₂CH₂OMe | SO₂Et | —CH(Me)— |
| 64 | t-Bu | H | i-Pr | Me | OCH₂CH₂OMe | SO₂Et | —CH(Me)— |
| 65 | Me | Me | i-Pr | Me | OCH₂CH₂OMe | SO₂Me | —CH(Me)— |
| 66 | Me | Et | Me | Me | OCH₂CH₂OMe | SO₂Me | —CH(Me)— |

TABLE 1-continued

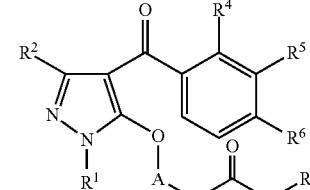

(I)

| No. | R¹ | R² | R³ | R⁴ | R⁵ | R⁶ | —A— |
|---|---|---|---|---|---|---|---|
| [HYO 3] ||||||||
| 67 | Me | Et | Et | Me | OCH$_2$CH$_2$OMe | SO$_2$Me | —CH(Me)— |
| 68 | Me | Et | i-Pr | Me | OCH$_2$CH$_2$OMe | SO$_2$Me | —CH(Me)— |
| 69 | Me | Et | n-Pr | Me | OCH$_2$CH$_2$OMe | SO$_2$Me | —CH(Me)— |
| 70 | Me | Et | n-Bu | Me | OCH$_2$CH$_2$OMe | SO$_2$Me | —CH(Me)— |
| 71 | Et | Et | Me | Me | OCH$_2$CH$_2$OMe | SO$_2$Me | —CH(Me)— |
| 72 | Et | Et | Et | Me | OCH$_2$CH$_2$OMe | SO$_2$Me | —CH(Me)— |
| 73 | Et | Et | i-Pr | Me | OCH$_2$CH$_2$OMe | SO$_2$Me | —CH(Me)— |
| 74 | Et | Et | n-Pr | Me | OCH$_2$CH$_2$OMe | SO$_2$Me | —CH(Me)— |
| 75 | Et | Et | n-Bu | Me | OCH$_2$CH$_2$OMe | SO$_2$Me | —CH(Me)— |
| 76 | i-Pr | Et | Me | Me | OCH$_2$CH$_2$OMe | SO$_2$Me | —CH(Me)— |
| 77 | i-Pr | Et | Et | Me | OCH$_2$CH$_2$OMe | SO$_2$Me | —CH(Me)— |
| 78 | i-Pr | Et | i-Pr | Me | OCH$_2$CH$_2$OMe | SO$_2$Me | —CH(Me)— |
| 79 | i-Pr | Et | n-Pr | Me | OCH$_2$CH$_2$OMe | SO$_2$Me | —CH(Me)— |
| 80 | i-Pr | Et | n-Bu | Me | OCH$_2$CH$_2$OMe | SO$_2$Me | —CH(Me)— |
| 81 | n-Pr | Et | Me | Me | OCH$_2$CH$_2$OMe | SO$_2$Me | —CH(Me)— |
| 82 | n-Pr | Et | Et | Me | OCH$_2$CH$_2$OMe | SO$_2$Me | —CH(Me)— |
| 83 | n-Pr | Et | i-Pr | Me | OCH$_2$CH$_2$OMe | SO$_2$Me | —CH(Me)— |
| 84 | n-Pr | Et | n-Pr | Me | OCH$_2$CH$_2$OMe | SO$_2$Me | —CH(Me)— |
| 85 | n-Pr | Et | n-Bu | Me | OCH$_2$CH$_2$OMe | SO$_2$Me | —CH(Me)— |
| 86 | n-Bu | Et | Me | Me | OCH$_2$CH$_2$OMe | SO$_2$Me | —CH(Me)— |
| 87 | n-Bu | Et | Et | Me | OCH$_2$CH$_2$OMe | SO$_2$Me | —CH(Me)— |
| 88 | n-Bu | Et | i-Pr | Me | OCH$_2$CH$_2$OMe | SO$_2$Me | —CH(Me)— |
| 89 | n-Bu | Et | n-Pr | Me | OCH$_2$CH$_2$OMe | SO$_2$Me | —CH(Me)— |
| 90 | n-Bu | Et | n-Bu | Me | OCH$_2$CH$_2$OMe | SO$_2$Me | —CH(Me)— |
| 91 | t-Bu | Et | Me | Me | OCH$_2$CH$_2$OMe | SO$_2$Me | —CH(Me)— |
| 92 | t-Bu | Et | Et | Me | OCH$_2$CH$_2$OMe | SO$_2$Me | —CH(Me)— |
| 93 | t-Bu | Et | i-Pr | Me | OCH$_2$CH$_2$OMe | SO$_2$Me | —CH(Me)— |
| 94 | t-Bu | Et | n-Pr | Me | OCH$_2$CH$_2$OMe | SO$_2$Me | —CH(Me)— |
| 95 | t-Bu | Et | n-Bu | Me | OCH$_2$CH$_2$OMe | SO$_2$Me | —CH(Me)— |
| 96 | Me | Et | Me | Cl | OCH$_2$CH$_2$OMe | SO$_2$Me | —CH(Me)— |
| 97 | Me | Et | Et | Cl | OCH$_2$CH$_2$OMe | SO$_2$Me | —CH(Me)— |
| 98 | Me | Et | i-Pr | Cl | OCH$_2$CH$_2$OMe | SO$_2$Me | —CH(Me)— |
| 99 | Me | Et | n-Pr | Cl | OCH$_2$CH$_2$OMe | SO$_2$Me | —CH(Me)— |
| 100 | Me | Et | n-Bu | Cl | OCH$_2$CH$_2$OMe | SO$_2$Me | —CH(Me)— |
| 101 | Et | Et | Me | Cl | OCH$_2$CH$_2$OMe | SO$_2$Me | —CH(Me)— |
| 102 | Et | Et | Et | Cl | OCH$_2$CH$_2$OMe | SO$_2$Me | —CH(Me)— |
| 103 | Et | Et | i-Pr | Cl | OCH$_2$CH$_2$OMe | SO$_2$Me | —CH(Me)— |
| 104 | Et | Et | n-Pr | Cl | OCH$_2$CH$_2$OMe | SO$_2$Me | —CH(Me)— |
| [HYO 4] ||||||||
| 105 | Et | Et | n-Bu | Cl | OCH$_2$CH$_2$OMe | SO$_2$Me | —CH(Me)— |
| 106 | i-Pr | Et | Me | Cl | OCH$_2$CH$_2$OMe | SO$_2$Me | —CH(Me)— |
| 107 | i-Pr | Et | Et | Cl | OCH$_2$CH$_2$OMe | SO$_2$Me | —CH(Me)— |
| 108 | i-Pr | Et | i-Pr | Cl | OCH$_2$CH$_2$OMe | SO$_2$Me | —CH(Me)— |
| 109 | i-Pr | Et | n-Pr | Cl | OCH$_2$CH$_2$OMe | SO$_2$Me | —CH(Me)— |
| 110 | i-Pr | Et | n-Bu | Cl | OCH$_2$CH$_2$OMe | SO$_2$Me | —CH(Me)— |
| 111 | n-Pr | Et | Me | Cl | OCH$_2$CH$_2$OMe | SO$_2$Me | —CH(Me)— |
| 112 | n-Pr | Et | Et | Cl | OCH$_2$CH$_2$OMe | SO$_2$Me | —CH(Me)— |
| 113 | n-Pr | Et | i-Pr | Cl | OCH$_2$CH$_2$OMe | SO$_2$Me | —CH(Me)— |
| 114 | n-Pr | Et | n-Pr | Cl | OCH$_2$CH$_2$OMe | SO$_2$Me | —CH(Me)— |
| 115 | n-Pr | Et | n-Bu | Cl | OCH$_2$CH$_2$OMe | SO$_2$Me | —CH(Me)— |
| 116 | n-Bu | Et | Me | Cl | OCH$_2$CH$_2$OMe | SO$_2$Me | —CH(Me)— |
| 117 | n-Bu | Et | Et | Cl | OCH$_2$CH$_2$OMe | SO$_2$Me | —CH(Me)— |
| 118 | n-Bu | Et | i-Pr | Cl | OCH$_2$CH$_2$OMe | SO$_2$Me | —CH(Me)— |
| 119 | n-Bu | Et | n-Pr | Cl | OCH$_2$CH$_2$OMe | SO$_2$Me | —CH(Me)— |
| 120 | n-Bu | Et | n-Bu | Cl | OCH$_2$CH$_2$OMe | SO$_2$Me | —CH(Me)— |
| 121 | t-Bu | Et | Me | Cl | OCH$_2$CH$_2$OMe | SO$_2$Me | —CH(Me)— |
| 122 | t-Bu | Et | Et | Cl | OCH$_2$CH$_2$OMe | SO$_2$Me | —CH(Me)— |
| 123 | t-Bu | Et | i-Pr | Cl | OCH$_2$CH$_2$OMe | SO$_2$Me | —CH(Me)— |
| 124 | t-Bu | Et | n-Pr | Cl | OCH$_2$CH$_2$OMe | SO$_2$Me | —CH(Me)— |
| 125 | t-Bu | Et | n-Bu | Cl | OCH$_2$CH$_2$OMe | SO$_2$Me | —CH(Me)— |
| 126 | Me | Et | Me | Me | OCH$_2$CF$_3$ | SO$_2$Me | —CH(Me)— |
| 127 | Me | Et | Et | Me | OCH$_2$CF$_3$ | SO$_2$Me | —CH(Me)— |
| 128 | Me | Et | i-Pr | Me | OCH$_2$CF$_3$ | SO$_2$Me | —CH(Me)— |

TABLE 1-continued

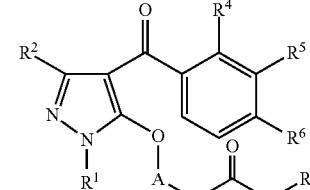

| No. | $R^1$ | $R^2$ | $R^3$ | $R^4$ | $R^5$ | $R^6$ | —A— |
|---|---|---|---|---|---|---|---|
| 129 | Me | Et | n-Pr | Me | OCH$_2$CF$_3$ | SO$_2$Me | —CH(Me)— |
| 130 | Me | Et | n-Bu | Me | OCH$_2$CF$_3$ | SO$_2$Me | —CH(Me)— |
| 131 | Et | Et | Me | Me | OCH$_2$CF$_3$ | SO$_2$Me | —CH(Me)— |
| 132 | Et | Et | Et | Me | OCH$_2$CF$_3$ | SO$_2$Me | —CH(Me)— |
| 133 | Et | Et | i-Pr | Me | OCH$_2$CF$_3$ | SO$_2$Me | —CH(Me)— |
| 134 | Et | Et | n-Pr | Me | OCH$_2$CF$_3$ | SO$_2$Me | —CH(Me)— |
| 135 | Et | Et | n-Bu | Me | OCH$_2$CF$_3$ | SO$_2$Me | —CH(Me)— |
| 136 | i-Pr | Et | Me | Me | OCH$_2$CF$_3$ | SO$_2$Me | —CH(Me)— |
| 137 | i-Pr | Et | Et | Me | OCH$_2$CF$_3$ | SO$_2$Me | —CH(Me)— |
| 138 | i-Pr | Et | i-Pr | Me | OCH$_2$CF$_3$ | SO$_2$Me | —CH(Me)— |
| 139 | i-Pr | Et | n-Pr | Me | OCH$_2$CF$_3$ | SO$_2$Me | —CH(Me)— |
| 140 | i-Pr | Et | n-Bu | Me | OCH$_2$CF$_3$ | SO$_2$Me | —CH(Me)— |
| 141 | n-Pr | Et | Me | Me | OCH$_2$CF$_3$ | SO$_2$Me | —CH(Me)— |
| 142 | n-Pr | Et | Et | Me | OCH$_2$CF$_3$ | SO$_2$Me | —CH(Me)— |
| [HYO 5] | | | | | | | |
| 143 | n-Pr | Et | i-Pr | Me | OCH$_2$CF$_3$ | SO$_2$Me | —CH(Me)— |
| 144 | n-Pr | Et | n-Pr | Me | OCH$_2$CF$_3$ | SO$_2$Me | —CH(Me)— |
| 145 | n-Pr | Et | n-Bu | Me | OCH$_2$CF$_3$ | SO$_2$Me | —CH(Me)— |
| 146 | n-Bu | Et | Me | Me | OCH$_2$CF$_3$ | SO$_2$Me | —CH(Me)— |
| 147 | n-Bu | Et | Et | Me | OCH$_2$CF$_3$ | SO$_2$Me | —CH(Me)— |
| 148 | n-Bu | Et | i-Pr | Me | OCH$_2$CF$_3$ | SO$_2$Me | —CH(Me)— |
| 149 | n-Bu | Et | n-Pr | Me | OCH$_2$CF$_3$ | SO$_2$Me | —CH(Me)— |
| 150 | n-Bu | Et | n-Bu | Me | OCH$_2$CF$_3$ | SO$_2$Me | —CH(Me)— |
| 151 | t-Bu | Et | Me | Me | OCH$_2$CF$_3$ | SO$_2$Me | —CH(Me)— |
| 152 | t-Bu | Et | Et | Me | OCH$_2$CF$_3$ | SO$_2$Me | —CH(Me)— |
| 153 | t-Bu | Et | i-Pr | Me | OCH$_2$CF$_3$ | SO$_2$Me | —CH(Me)— |
| 154 | t-Bu | Et | n-Pr | Me | OCH$_2$CF$_3$ | SO$_2$Me | —CH(Me)— |
| 155 | t-Bu | Et | n-Bu | Me | OCH$_2$CF$_3$ | SO$_2$Me | —CH(Me)— |
| 156 | Me | Et | Me | Cl | OCH$_2$CF$_3$ | SO$_2$Me | —CH(Me)— |
| 157 | Me | Et | Et | Cl | OCH$_2$CF$_3$ | SO$_2$Me | —CH(Me)— |
| 158 | Me | Et | i-Pr | Cl | OCH$_2$CF$_3$ | SO$_2$Me | —CH(Me)— |
| 159 | Me | Et | n-Pr | Cl | OCH$_2$CF$_3$ | SO$_2$Me | —CH(Me)— |
| 160 | Me | Et | n-Bu | Cl | OCH$_2$CF$_3$ | SO$_2$Me | —CH(Me)— |
| 161 | Et | Et | Me | Cl | OCH$_2$CF$_3$ | SO$_2$Me | —CH(Me)— |
| 162 | Et | Et | Et | Cl | OCH$_2$CF$_3$ | SO$_2$Me | —CH(Me)— |
| 163 | Et | Et | i-Pr | Cl | OCH$_2$CF$_3$ | SO$_2$Me | —CH(Me)— |
| 164 | Et | Et | n-Pr | Cl | OCH$_2$CF$_3$ | SO$_2$Me | —CH(Me)— |
| 165 | Et | Et | n-Bu | Cl | OCH$_2$CF$_3$ | SO$_2$Me | —CH(Me)— |
| 166 | i-Pr | Et | Me | Cl | OCH$_2$CF$_3$ | SO$_2$Me | —CH(Me)— |
| 167 | i-Pr | Et | Et | Cl | OCH$_2$CF$_3$ | SO$_2$Me | —CH(Me)— |
| 168 | i-Pr | Et | i-Pr | Cl | OCH$_2$CF$_3$ | SO$_2$Me | —CH(Me)— |
| 169 | i-Pr | Et | n-Pr | Cl | OCH$_2$CF$_3$ | SO$_2$Me | —CH(Me)— |
| 170 | i-Pr | Et | n-Bu | Cl | OCH$_2$CF$_3$ | SO$_2$Me | —CH(Me)— |
| 171 | n-Pr | Et | Me | Cl | OCH$_2$CF$_3$ | SO$_2$Me | —CH(Me)— |
| 172 | n-Pr | Et | Et | Cl | OCH$_2$CF$_3$ | SO$_2$Me | —CH(Me)— |
| 173 | n-Pr | Et | i-Pr | Cl | OCH$_2$CF$_3$ | SO$_2$Me | —CH(Me)— |
| 174 | n-Pr | Et | n-Pr | Cl | OCH$_2$CF$_3$ | SO$_2$Me | —CH(Me)— |
| 175 | n-Pr | Et | n-Bu | Cl | OCH$_2$CF$_3$ | SO$_2$Me | —CH(Me)— |
| 176 | n-Bu | Et | Me | Cl | OCH$_2$CF$_3$ | SO$_2$Me | —CH(Me)— |
| 177 | n-Bu | Et | Et | Cl | OCH$_2$CF$_3$ | SO$_2$Me | —CH(Me)— |
| 178 | n-Bu | Et | i-Pr | Cl | OCH$_2$CF$_3$ | SO$_2$Me | —CH(Me)— |
| 179 | n-Bu | Et | n-Pr | Cl | OCH$_2$CF$_3$ | SO$_2$Me | —CH(Me)— |
| 180 | n-Bu | Et | n-Bu | Cl | OCH$_2$CF$_3$ | SO$_2$Me | —CH(Me)— |
| [HYO 6] | | | | | | | |
| 181 | t-Bu | Et | Me | Cl | OCH$_2$CF$_3$ | SO$_2$Me | —CH(Me)— |
| 182 | t-Bu | Et | Et | Cl | OCH$_2$CF$_3$ | SO$_2$Me | —CH(Me)— |
| 183 | t-Bu | Et | i-Pr | Cl | OCH$_2$CF$_3$ | SO$_2$Me | —CH(Me)— |
| 184 | t-Bu | Et | n-Pr | Cl | OCH$_2$CF$_3$ | SO$_2$Me | —CH(Me)— |
| 185 | t-Bu | Et | n-Bu | Cl | OCH$_2$CF$_3$ | SO$_2$Me | —CH(Me)— |
| 186 | Me | Et | Me | Me | CH$_2$OMe | SO$_2$Me | —CH(Me)— |
| 187 | Me | Et | Et | Me | CH$_2$OMe | SO$_2$Me | —CH(Me)— |
| 188 | Me | Et | i-Pr | Me | CH$_2$OMe | SO$_2$Me | —CH(Me)— |
| 189 | Me | Et | n-Pr | Me | CH$_2$OMe | SO$_2$Me | —CH(Me)— |
| 190 | Me | Et | n-Bu | Me | CH$_2$OMe | SO$_2$Me | —CH(Me)— |

TABLE 1-continued

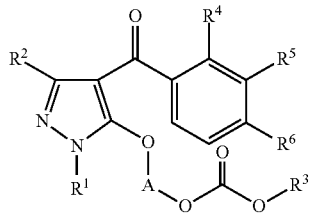

(I)

| No. | R¹ | R² | R³ | R⁴ | R⁵ | R⁶ | —A— |
|---|---|---|---|---|---|---|---|
| 191 | Et | Et | Me | Me | CH₂OMe | SO₂Me | —CH(Me)— |
| 192 | Et | Et | Et | Me | CH₂OMe | SO₂Me | —CH(Me)— |
| 193 | Et | Et | i-Pr | Me | CH₂OMe | SO₂Me | —CH(Me)— |
| 194 | Et | Et | n-Pr | Me | CH₂OMe | SO₂Me | —CH(Me)— |
| 195 | Et | Et | n-Bu | Me | CH₂OMe | SO₂Me | —CH(Me)— |
| 196 | i-Pr | Et | Me | Me | CH₂OMe | SO₂Me | —CH(Me)— |
| 197 | i-Pr | Et | Et | Me | CH₂OMe | SO₂Me | —CH(Me)— |
| 198 | i-Pr | Et | i-Pr | Me | CH₂OMe | SO₂Me | —CH(Me)— |
| 199 | i-Pr | Et | n-Pr | Me | CH₂OMe | SO₂Me | —CH(Me)— |
| 200 | i-Pr | Et | n-Bu | Me | CH₂OMe | SO₂Me | —CH(Me)— |
| 201 | n-Pr | Et | Me | Me | CH₂OMe | SO₂Me | —CH(Me)— |
| 202 | n-Pr | Et | Et | Me | CH₂OMe | SO₂Me | —CH(Me)— |
| 203 | n-Pr | Et | i-Pr | Me | CH₂OMe | SO₂Me | —CH(Me)— |
| 204 | n-Pr | Et | n-Pr | Me | CH₂OMe | SO₂Me | —CH(Me)— |
| 205 | n-Pr | Et | n-Bu | Me | CH₂OMe | SO₂Me | —CH(Me)— |
| 206 | n-Bu | Et | Me | Me | CH₂OMe | SO₂Me | —CH(Me)— |
| 207 | n-Bu | Et | Et | Me | CH₂OMe | SO₂Me | —CH(Me)— |
| 208 | n-Bu | Et | i-Pr | Me | CH₂OMe | SO₂Me | —CH(Me)— |
| 209 | n-Bu | Et | n-Pr | Me | CH₂OMe | SO₂Me | —CH(Me)— |
| 210 | n-Bu | Et | n-Bu | Me | CH₂OMe | SO₂Me | —CH(Me)— |
| 211 | t-Bu | Et | Me | Me | CH₂OMe | SO₂Me | —CH(Me)— |
| 212 | t-Bu | Et | Et | Me | CH₂OMe | SO₂Me | —CH(Me)— |
| 213 | t-Bu | Et | i-Pr | Me | CH₂OMe | SO₂Me | —CH(Me)— |
| 214 | t-Bu | Et | n-Pr | Me | CH₂OMe | SO₂Me | —CH(Me)— |
| 215 | t-Bu | Et | n-Bu | Me | CH₂OMe | SO₂Me | —CH(Me)— |
| 216 | Me | Et | Me | Cl | CH₂OMe | SO₂Me | —CH(Me)— |

[HYO 7]

| No. | R¹ | R² | R³ | R⁴ | R⁵ | R⁶ | —A— |
|---|---|---|---|---|---|---|---|
| 217 | Me | Et | Et | Cl | CH₂OMe | SO₂Me | —CH(Me)— |
| 218 | Me | Et | i-Pr | Cl | CH₂OMe | SO₂Me | —CH(Me)— |
| 219 | Me | Et | n-Pr | Cl | CH₂OMe | SO₂Me | —CH(Me)— |
| 220 | Me | Et | n-Bu | Cl | CH₂OMe | SO₂Me | —CH(Me)— |
| 221 | Et | Et | Me | Cl | CH₂OMe | SO₂Me | —CH(Me)— |
| 222 | Et | Et | Et | Cl | CH₂OMe | SO₂Me | —CH(Me)— |
| 223 | Et | Et | i-Pr | Cl | CH₂OMe | SO₂Me | —CH(Me)— |
| 224 | Et | Et | n-Pr | Cl | CH₂OMe | SO₂Me | —CH(Me)— |
| 225 | Et | Et | n-Bu | Cl | CH₂OMe | SO₂Me | —CH(Me)— |
| 226 | i-Pr | Et | Me | Cl | CH₂OMe | SO₂Me | —CH(Me)— |
| 227 | i-Pr | Et | Et | Cl | CH₂OMe | SO₂Me | —CH(Me)— |
| 228 | i-Pr | Et | i-Pr | Cl | CH₂OMe | SO₂Me | —CH(Me)— |
| 229 | i-Pr | Et | n-Pr | Cl | CH₂OMe | SO₂Me | —CH(Me)— |
| 230 | i-Pr | Et | n-Bu | Cl | CH₂OMe | SO₂Me | —CH(Me)— |
| 231 | n-Pr | Et | Me | Cl | CH₂OMe | SO₂Me | —CH(Me)— |
| 232 | n-Pr | Et | Et | Cl | CH₂OMe | SO₂Me | —CH(Me)— |
| 233 | n-Pr | Et | i-Pr | Cl | CH₂OMe | SO₂Me | —CH(Me)— |
| 234 | n-Pr | Et | n-Pr | Cl | CH₂OMe | SO₂Me | —CH(Me)— |
| 235 | n-Pr | Et | n-Bu | Cl | CH₂OMe | SO₂Me | —CH(Me)— |
| 236 | n-Bu | Et | Me | Cl | CH₂OMe | SO₂Me | —CH(Me)— |
| 237 | n-Bu | Et | Et | Cl | CH₂OMe | SO₂Me | —CH(Me)— |
| 238 | n-Bu | Et | i-Pr | Cl | CH₂OMe | SO₂Me | —CH(Me)— |
| 239 | n-Bu | Et | n-Pr | Cl | CH₂OMe | SO₂Me | —CH(Me)— |
| 240 | n-Bu | Et | n-Bu | Cl | CH₂OMe | SO₂Me | —CH(Me)— |
| 241 | t-Bu | Et | Me | Cl | CH₂OMe | SO₂Me | —CH(Me)— |
| 242 | t-Bu | Et | Et | Cl | CH₂OMe | SO₂Me | —CH(Me)— |
| 243 | t-Bu | Et | i-Pr | Cl | CH₂OMe | SO₂Me | —CH(Me)— |
| 244 | t-Bu | Et | n-Pr | Cl | CH₂OMe | SO₂Me | —CH(Me)— |
| 245 | t-Bu | Et | n-Bu | Cl | CH₂OMe | SO₂Me | —CH(Me)— |
| 246 | Me | Et | Me | Me | CH₂OMe | SO₂Me | —CH(Me)— |
| 247 | Me | Et | Et | Me | CH₂OMe | SO₂Me | —CH(Me)— |
| 248 | Me | Et | i-Pr | Me | CH₂OMe | SO₂Me | —CH(Me)— |
| 249 | Me | Et | n-Pr | Me | CH₂OMe | SO₂Me | —CH(Me)— |
| 250 | Me | Et | n-Bu | Me | CH₂OMe | SO₂Me | —CH(Me)— |
| 251 | Et | Et | Me | Me | CH₂OMe | SO₂Me | —CH(Me)— |

TABLE 1-continued (I)

| No. | R¹ | R² | R³ | R⁴ | R⁵ | R⁶ | —A— |
|---|---|---|---|---|---|---|---|
| | | | | | [HYO 8] | | |
| 252 | Et | Et | Et | Me | C(O)OMe | SO₂Me | —CH(Me)— |
| 253 | Et | Et | i-Pr | Me | C(O)OMe | SO₂Me | —CH(Me)— |
| 254 | Et | Et | n-Pr | Me | C(O)OMe | SO₂Me | —CH(Me)— |
| 255 | Et | Et | n-Bu | Me | C(O)OMe | SO₂Me | —CH(Me)— |
| 256 | i-Pr | Et | Me | Me | C(O)OMe | SO₂Me | —CH(Me)— |
| 257 | i-Pr | Et | Et | Me | C(O)OMe | SO₂Me | —CH(Me)— |
| 258 | i-Pr | Et | i-Pr | Me | C(O)OMe | SO₂Me | —CH(Me)— |
| 259 | i-Pr | Et | n-Pr | Me | C(O)OMe | SO₂Me | —CH(Me)— |
| 260 | i-Pr | Et | n-Bu | Me | C(O)OMe | SO₂Me | —CH(Me)— |
| 261 | n-Pr | Et | Me | Me | C(O)OMe | SO₂Me | —CH(Me)— |
| 262 | n-Pr | Et | Et | Me | C(O)OMe | SO₂Me | —CH(Me)— |
| 263 | n-Pr | Et | i-Pr | Me | C(O)OMe | SO₂Me | —CH(Me)— |
| 264 | n-Pr | Et | n-Pr | Me | C(O)OMe | SO₂Me | —CH(Me)— |
| 265 | n-Pr | Et | n-Bu | Me | C(O)OMe | SO₂Me | —CH(Me)— |
| 266 | n-Bu | Et | Me | Me | C(O)OMe | SO₂Me | —CH(Me)— |
| 267 | n-Bu | Et | Et | Me | C(O)OMe | SO₂Me | —CH(Me)— |
| 268 | n-Bu | Et | i-Pr | Me | C(O)OMe | SO₂Me | —CH(Me)— |
| 269 | n-Bu | Et | n-Pr | Me | C(O)OMe | SO₂Me | —CH(Me)— |
| 270 | n-Bu | Et | n-Bu | Me | C(O)OMe | SO₂Me | —CH(Me)— |
| 271 | t-Bu | Et | Me | Me | C(O)OMe | SO₂Me | —CH(Me)— |
| 272 | t-Bu | Et | Et | Me | C(O)OMe | SO₂Me | —CH(Me)— |
| 273 | t-Bu | Et | i-Pr | Me | C(O)OMe | SO₂Me | —CH(Me)— |
| 274 | t-Bu | Et | n-Pr | Me | C(O)OMe | SO₂Me | —CH(Me)— |
| 275 | t-Bu | Et | n-Bu | Me | C(O)OMe | SO₂Me | —CH(Me)— |
| 276 | Me | Et | Me | Cl | C(O)OMe | SO₂Me | —CH(Me)— |
| 277 | Me | Et | Et | Cl | C(O)OMe | SO₂Me | —CH(Me)— |
| 278 | Me | Et | i-Pr | Cl | C(O)OMe | SO₂Me | —CH(Me)— |
| 279 | Me | Et | n-Pr | Cl | C(O)OMe | SO₂Me | —CH(Me)— |
| 280 | Me | Et | n-Bu | Cl | C(O)OMe | SO₂Me | —CH(Me)— |
| 281 | Et | Et | Me | Cl | C(O)OMe | SO₂Me | —CH(Me)— |
| 282 | Et | Et | Et | Cl | C(O)OMe | SO₂Me | —CH(Me)— |
| 283 | Et | Et | i-Pr | Cl | C(O)OMe | SO₂Me | —CH(Me)— |
| 284 | Et | Et | n-Pr | Cl | C(O)OMe | SO₂Me | —CH(Me)— |
| 285 | Et | Et | n-Bu | Cl | C(O)OMe | SO₂Me | —CH(Me)— |
| 286 | i-Pr | Et | Me | Cl | C(O)OMe | SO₂Me | —CH(Me)— |
| 287 | i-Pr | Et | Et | Cl | C(O)OMe | SO₂Me | —CH(Me)— |
| | | | | | [HYO 9] | | |
| 288 | i-Pr | Et | i-Pr | Cl | C(O)OMe | SO₂Me | —CH(Me)— |
| 289 | i-Pr | Et | n-Pr | Cl | C(O)OMe | SO₂Me | —CH(Me)— |
| 290 | i-Pr | Et | n-Bu | Cl | C(O)OMe | SO₂Me | —CH(Me)— |
| 291 | n-Pr | Et | Me | Cl | C(O)OMe | SO₂Me | —CH(Me)— |
| 292 | n-Pr | Et | Et | Cl | C(O)OMe | SO₂Me | —CH(Me)— |
| 293 | n-Pr | Et | i-Pr | Cl | C(O)OMe | SO₂Me | —CH(Me)— |
| 294 | n-Pr | Et | n-Pr | Cl | C(O)OMe | SO₂Me | —CH(Me)— |
| 295 | n-Pr | Et | n-Bu | Cl | C(O)OMe | SO₂Me | —CH(Me)— |
| 296 | n-Bu | Et | Me | Cl | C(O)OMe | SO₂Me | —CH(Me)— |
| 297 | n-Bu | Et | Et | Cl | C(O)OMe | SO₂Me | —CH(Me)— |
| 298 | n-Bu | Et | i-Pr | Cl | C(O)OMe | SO₂Me | —CH(Me)— |
| 299 | n-Bu | Et | n-Pr | Cl | C(O)OMe | SO₂Me | —CH(Me)— |
| 300 | n-Bu | Et | n-Bu | Cl | C(O)OMe | SO₂Me | —CH(Me)— |
| 301 | t-Bu | Et | Me | Cl | C(O)OMe | SO₂Me | —CH(Me)— |
| 302 | t-Bu | Et | Et | Cl | C(O)OMe | SO₂Me | —CH(Me)— |
| 303 | t-Bu | Et | i-Pr | Cl | C(O)OMe | SO₂Me | —CH(Me)— |
| 304 | t-Bu | Et | n-Pr | Cl | C(O)OMe | SO₂Me | —CH(Me)— |
| 305 | t-Bu | Et | n-Bu | Cl | C(O)OMe | SO₂Me | —CH(Me)— |
| 306 | Me | H | Et | Me | CH₂OCH(Me)₂ | SO₂Me | —CH(Me)— |
| 307 | Et | H | Et | Me | CH₂OCH(Me)₂ | SO₂Me | —CH(Me)— |
| 308 | n-Pr | H | Et | Me | CH₂OCH(Me)₂ | SO₂Me | —CH(Me)— |
| 309 | i-Pr | H | Et | Me | CH₂OCH(Me)₂ | SO₂Me | —CH(Me)— |
| 310 | Me | H | Et | Cl | CH₂OCH(Me)₂ | SO₂Me | —CH(Me)— |
| 311 | Et | H | Et | Cl | CH₂OCH(Me)₂ | SO₂Me | —CH(Me)— |
| 312 | n-Pr | H | Et | Cl | CH₂OCH(Me)₂ | SO₂Me | —CH(Me)— |
| 313 | i-Pr | H | Et | Cl | CH₂OCH(Me)₂ | SO₂Me | —CH(Me)— |

TABLE 1-continued $$\text{(I)}$$

Structure: pyrazole with R¹ on N, R² on ring, connected via O-A-O-C(=O)-O-R³ linkage and C(=O) to phenyl ring bearing R⁴, R⁵, R⁶.

| No. | R¹ | R² | R³ | R⁴ | R⁵ | R⁶ | —A— |
|---|---|---|---|---|---|---|---|
| 314 | Me | H | Me | Me | $CH_2OEt$ | $SO_2Me$ | —CH(Me)— |
| 315 | Me | H | Me | Me | C(O)OMe | $SO_2Me$ | —CH(Me)— |
| 316 | Me | H | Me | Me | $CH_2OMe$ | $SO_2Me$ | —CH(Me)— |
| 317 | Me | H | Et | Me | $CH_2OEt$ | $SO_2Me$ | —CH(Me)— |
| 318 | Me | H | Et | Me | $OCH_2CH_2OCH(Me)_2$ | $SO_2Me$ | —CH(Me)— |
| 319 | Me | Me | Me | Me | $OCH_2CH_2OMe$ | $SO_2Me$ | —CH(Me)— |
| 320 | Me | H | i-Pr | Me | $OCH_2CH_2OMe$ | $SO_2Me$ | —CH(Me)— |
| 321 | Et | H | Et | Me | C(O)OMe | $SO_2Me$ | —CH(Me)— |
| 322 | Et | Me | Et | Me | $OCH_2CH_2OMe$ | $SO_2Me$ | —CH(Me)— |
| 323 | n-Pr | H | Et | Me | $OCH_2CH_2OMe$ | $SO_2Me$ | —CH(Me)— |
| 324 | i-Pr | H | Me | Me | $OCH_2CH_2OMe$ | $SO_2Me$ | —CH(Me)— |

EXAMPLE(S)

Example 1

Upland field soil was put into a 1/1,000,000 hectare pot, and seeds of various plants were sown. When the respective plants reached predetermined leaf stage, herbicidal compositions in predetermined amounts were diluted with water in an amount corresponding to 300 L/ha and applied for foliar treatment by a small sprayer.

On the 7 to 24 days after treatment, the state of growth of the respective plants was visually observed to determine the growth inhibition rate (measured value) in accordance with the following evaluation standard. Further, in accordance with the above Colby's formula, the growth inhibition rate (calculated value) was calculated. The results are shown in Tables 2-1 to 2-119. In Tables, with respect to the compound Q, Compound Nos. in Table 1 are described, and with respect to other herbicidal compounds, common names are described.

Growth inhibition rate (%)=0: equivalent to the non-treated area to 100: complete kill

TABLE 2-1

[HYO 10]

| Compound | Active ingredient amount (g/ha) | Growth inhibition rate (%) of crabgrass (3.5 to 4.3 leaf stage) (21 days after treatment) Measured value | Calculated value |
|---|---|---|---|
| NO. 1 | 5 | 78 | — |
| Nicosulfuron | 10 | 30 | — |
| NO. 1 + nicosulfuron | 5 + 10 | 85 | 84.6 |

TABLE 2-2

[HYO 11]

| Compound | Active ingredient amount (g/ha) | Growth inhibition rate (%) of prickly sida (2.1 to 3.1 leaf stage) (21 days after treatment) Measured value | Calculated value |
|---|---|---|---|
| NO. 1 | 50 | 45 | — |
| Nicosulfuron | 50 | 70 | — |
|  | 30 | 50 | — |
|  | 20 | 40 | — |
|  | 10 | 10 | — |
|  | 5 | 0 | — |
|  | 2.5 | 0 | — |
| NO. 1 + nicosulfuron | 50 + 50 | 85 | 84 |
|  | 50 + 30 | 85 | 73 |
|  | 50 + 20 | 78 | 67 |
|  | 50 + 10 | 65 | 51 |
|  | 50 + 5 | 75 | 45 |
|  | 50 + 2.5 | 65 | 45 |

TABLE 2-3

[HYO 12]

| Compound | Active ingredient amount (g/ha) | Growth inhibition rate (%) of crabgrass (3.5 to 4.3 leaf stage) (21 days after treatment) Measured value | Calculated value |
|---|---|---|---|
| NO. 1 | 5 | 78 | — |
| Atrazine | 175 | 0 | — |
| NO. 1 + atrazine | 5 + 175 | 99 | 78 |

TABLE 2-4

[HYO 13]

| Compound | Active ingredient amount (g/ha) | Growth inhibition rate (%) of velvetleaf (3.0-3.8 leaf stage) (21 days after treatment) Measured value | Calculated value |
| --- | --- | --- | --- |
| NO. 1 | 5 | 88 | — |
| Atrazine | 175 | 0 | — |
| NO. 1 + atrazine | 5 + 175 | 97 | 88 |

TABLE 2-5

[HYO 14]

| Compound | Active ingredient amount (g/ha) | Growth inhibition rate (%) of crabgrass (3.5 to 4.3 leaf stage) (21 days after treatment) Measured value | Calculated value |
| --- | --- | --- | --- |
| NO. 1 | 5 | 78 | — |
| Terbuthylazine | 175 | 0 | — |
| NO. 1 + terbuthylazine | 5 + 175 | 94 | 78 |

TABLE 2-6

[HYO 15]

| Compound | Active ingredient amount (g/ha) | Growth inhibition rate (%) of velvetleaf (3.0-3.8 leaf stage) (21 days after treatment) Measured value | Calculated value |
| --- | --- | --- | --- |
| NO. 1 | 5 | 88 | — |
| Terbuthylazine | 175 | 0 | — |
| NO. 1 + terbuthylazine | 5 + 175 | 97 | 88 |

TABLE 2-7

[HYO 16]

| Compound | Active ingredient amount (g/ha) | Growth inhibition rate (%) of crabgrass (3.5 to 4.3 leaf stage) (21 days after treatment) Measured value | Calculated value |
| --- | --- | --- | --- |
| NO. 1 | 5 | 78 | — |
| Acetochlor | 400 | 0 | — |
| NO. 1 + acetochlor | 5 + 400 | 93 | 78 |

TABLE 2-8

[HYO 17]

| Compound | Active ingredient amount (g/ha) | Growth inhibition rate (%) of velvetleaf (3.0-3.8 leaf stage) (21 days after treatment) Measured value | Calculated value |
| --- | --- | --- | --- |
| NO. 1 | 5 | 88 | — |
| Acetochlor | 400 | 0 | — |

TABLE 2-8-continued

[HYO 17]

| Compound | Active ingredient amount (g/ha) | Growth inhibition rate (%) of velvetleaf (3.0-3.8 leaf stage) (21 days after treatment) Measured value | Calculated value |
| --- | --- | --- | --- |
| NO. 1 + acetochlor | 5 + 400 | 95 | 88 |

TABLE 2-9

[HYO 18]

| Compound | Active ingredient amount (g/ha) | Growth inhibition rate (%) of crabgrass (3.5 to 4.3 leaf stage) (21 days after treatment) Measured value | Calculated value |
| --- | --- | --- | --- |
| NO. 1 | 5 | 78 | — |
| S-Metolachlor | 400 | 0 | — |
| NO. 1 + S-metolachlor | 5 + 400 | 88 | 78 |

TABLE 2-10

[HYO 19]

| Compound | Active ingredient amount (g/ha) | Growth inhibition rate (%) of velvetleaf (3.0-3.8 leaf stage) (21 days after treatment) Measured value | Calculated value |
| --- | --- | --- | --- |
| NO. 1 | 5 | 88 | — |
| S-Metolachlor | 400 | 0 | — |
| NO. 1 + S-metolachlor | 5 + 400 | 93 | 88 |

TABLE 2-11

[HYO 20]

| Compound | Active ingredient amount (g/ha) | Growth inhibition rate (%) of crabgrass (4.5-5.1 leaf stage) (21 days after treatment) Measured value | Calculated value |
| --- | --- | --- | --- |
| NO. 2 | 1.875 | 40 | — |
| Nicosulfuron | 80 | 94 | — |
|  | 20 | 50 | — |
| NO. 2 + nicosulfuron | 1.875 + 80 | 99 | 96 |
|  | 1.875 + 20 | 85 | 70 |

TABLE 2-12

[HYO 21]

| Compound | Active ingredient amount (g/ha) | Growth inhibition rate (%) of velvetleaf (4.0-4.4 leaf stage) (22 days after treatment) Measured value | Calculated value |
| --- | --- | --- | --- |
| NO. 2 | 7 | 80 | — |
| Nicosulfuron | 10 | 40 | — |
| NO. 2 + nicosulfuron | 7 + 10 | 95 | 88 |

TABLE 2-13

[HYO 22]

| Compound | Active ingredient amount (g/ha) | Growth inhibition rate (%) of velvetleaf (4.0-4.5 leaf stage) (21 days after treatment) | |
|---|---|---|---|
| | | Measured value | Calculated value |
| NO. 2 | 1.875 | 40 | — |
| Nicosulfuron | 80 | 83 | — |
| | 60 | 70 | — |
| | 40 | 65 | — |
| NO. 2 + nicosulfuron | 1.875 + 80 | 92 | 90 |
| | 1.875 + 60 | 93 | 82 |
| | 1.875 + 40 | 80 | 79 |

TABLE 2-14

[HYO 23]

| Compound | Active ingredient amount (g/ha) | Growth inhibition rate (%) of crabgrass (3.1-4.0 leaf stage) (22 days after treatment) | |
|---|---|---|---|
| | | Measured value | Calculated value |
| NO. 2 | 15 | 85 | — |
| Atrazine | 375 | 0 | — |
| NO 2 + atrazine | 15 + 375 | 95 | 85 |

TABLE 2-15

[HYO 24]

| Compound | Active ingredient amount (g/ha) | Growth inhibition rate (%) of crabgrass (5.0-6.0 leaf stage) (14 days after treatment) | |
|---|---|---|---|
| | | Measured value | Calculated value |
| NO. 2 | 3.75 | 60 | — |
| Atrazine | 2000 | 25 | — |
| | 1000 | 10 | — |
| | 500 | 0 | — |
| NO. 2 + atrazine | 3.75 + 2000 | 99 | 70 |
| | 3.75 + 1000 | 97 | 64 |
| | 3.75 + 500 | 70 | 60 |

TABLE 2-16

[HYO 25]

| Compound | Active ingredient amount (g/ha) | Growth inhibition rate (%) of velvetleaf (4.0-4.4 leaf stage) (22 days after treatment) | |
|---|---|---|---|
| | | Measured value | Calculated value |
| NO. 2 | 15 | 85 | — |
| Atrazine | 375 | 25 | — |
| NO. 2 + atrazine | 15 + 375 | 100 | 89 |

TABLE 2-17

[HYO 26]

| Compound | Active ingredient amount (g/ha) | Growth inhibition rate (%) of velvetleaf (4.6-5.3 leaf stage) (14 days after treatment) | |
|---|---|---|---|
| | | Measured value | Calculated value |
| NO. 2 | 1.875 | 65 | — |
| Atrazine | 2000 | 70 | — |
| | 1000 | 60 | — |
| | 500 | 45 | — |
| NO 2 + atrazine | 1.875 + 2000 | 100 | 90 |
| | 1.875 + 1000 | 100 | 86 |
| | 1.875 + 500 | 100 | 81 |

TABLE 2-18

[HYO 27]

| Compound | Active ingredient amount (g/ha) | Growth inhibition rate (%) of prickly sida (3.0-3.3 leaf stage) (21 days after treatment) | |
|---|---|---|---|
| | | Measured value | Calculated value |
| NO. 2 | 50 | 60 | — |
| Atrazine | 250 | 65 | — |
| | 125 | 45 | — |
| | 63 | 30 | — |
| NO. 2 + atrazine | 50 + 250 | 100 | 86 |
| | 50 + 125 | 100 | 78 |
| | 50 + 63 | 100 | 72 |

TABLE 2-19

[HYO 28]

| Compound | Active ingredient amount (g/ha) | Growth inhibition rate (%) of crabgrass (3.1-4.0 leaf stage) (22 days after treatment) | |
|---|---|---|---|
| | | Measured value | Calculated value |
| NO. 2 | 15 | 85 | — |
| Terbuthylazine | 375 | 0 | — |
| NO. 2 + terbuthylazine | 15 + 375 | 95 | 85 |

TABLE 2-20

[HYO 29]

| Compound | Active ingredient amount (g/ha) | Growth inhibition rate (%) of velvetleaf (4.0-4.4 leaf stage) (22 days after treatment) | |
|---|---|---|---|
| | | Measured value | Calculated value |
| NO. 2 | 7 | 80 | — |
| Terbuthylazine | 175 | 15 | — |
| NO. 2 + terbuthylazine | 7 + 175 | 100 | 83 |

TABLE 2-21

[HYO 30]

| Compound | Active ingredient amount (g/ha) | Growth inhibition rate (%) of velvetleaf (4.0-4.5 leaf stage) (21 days after treatment) | |
|---|---|---|---|
| | | Measured value | Calculated value |
| NO. 2 | 3.75 | 55 | — |
| Terbuthylazine | 2000 | 55 | — |
| | 1000 | 45 | — |
| | 500 | 30 | — |
| NO. 2 + terbuthylazine | 3.75 + 2000 | 100 | 80 |
| | 3.75 + 1000 | 100 | 75 |
| | 3.75 + 500 | 100 | 69 |

TABLE 2-22

[HYO 31]

| Compound | Active ingredient amount (g/ha) | Growth inhibition rate (%) of prickly sida (3.0-4.0 leaf stage) (21 days after treatment) | |
|---|---|---|---|
| | | Measured value | Calculated value |
| NO. 2 | 100 | 35 | — |
| Terbuthylazine | 250 | 20 | — |
| | 125 | 0 | — |
| | 63 | 0 | — |
| NO. 2 + terbuthylazine | 100 + 250 | 85 | 48 |
| | 100 + 125 | 83 | 35 |
| | 100 + 63 | 55 | 35 |

TABLE 2-23

[HYO 32]

| Compound | Active ingredient amount (g/ha) | Growth inhibition rate (%) of prickly sida (3.0-3.3 leaf stage) (14 days after treatment) | |
|---|---|---|---|
| | | Measured value | Calculated value |
| NO. 2 | 75 | 65 | — |
| Acetochlor | 800 | 30 | — |
| | 400 | 10 | — |
| | 200 | 0 | — |
| | 100 | 0 | — |
| NO. 2 + acetochlor | 75 + 800 | 80 | 76 |
| | 75 + 400 | 83 | 69 |
| | 75 + 200 | 70 | 65 |
| | 75 + 100 | 80 | 65 |

TABLE 2-24

[HYO 33]

| Compound | Active ingredient amount (g/ha) | Growth inhibition rate (%) of crabgrass (5.0-6.0 leaf stage) (14 days after treatment) | |
|---|---|---|---|
| | | Measured value | Calculated value |
| NO. 2 | 3.75 | 60 | — |
| S-Metolachlor | 800 | 0 | — |
| NO. 2 + S-metolachlor | 3.75 + 800 | 65 | 60 |

TABLE 2-25

[HYO 34]

| Compound | Active ingredient amount (g/ha) | Growth inhibition rate (%) of velvetleaf (4.6-5.3 leaf stage) (14 days after treatment) | |
|---|---|---|---|
| | | Measured value | Calculated value |
| NO. 2 | 15 | 88 | — |
| S-Metolachlor | 1200 | 0 | — |
| NO. 2 + S-metolachlor | 15 + 1200 | 95 | 88 |

TABLE 2-26

[HYO 35]

| Compound | Active ingredient amount (g/ha) | Growth inhibition rate (%) of prickly sida (3.0-3.3 leaf stage) (21 days after treatment) | |
|---|---|---|---|
| | | Measured value | Calculated value |
| NO. 2 | 100 | 88 | — |
| S-Metolachlor | 800 | 20 | — |
| NO. 2 + S-metolachlor | 100 + 800 | 100 | 90 |

TABLE 2-27

[HYO 36]

| Compound | Active ingredient amount (g/ha) | Growth inhibition rate (%) of crabgrass (3.1-4.0 leaf stage) (22 days after treatment) | |
|---|---|---|---|
| | | Measured value | Calculated value |
| NO. 2 | 7 | 68 | — |
| Bromoxynil-octanoate | 77 | 0 | — |
| NO. 2 + bromoxynil-octanoate | 7 + 77 | 75 | 68 |

TABLE 2-28

[HYO 37]

| Compound | Active ingredient amount (g/ha) | Growth inhibition rate (%) of velvetleaf (4.0-4.3 leaf stage) (22 days after treatment) | |
|---|---|---|---|
| | | Measured value | Calculated value |
| NO. 2 | 3.75 | 0 | — |
| Bromoxynil-octanoate | 100 | 25 | — |
| NO. 2 + bromoxynil-octanoate | 3.75 + 100 | 100 | 25 |

TABLE 2-29

[HYO 38]

| Compound | Active ingredient amount (g/ha) | Growth inhibition rate (%) of pricky sida (3.0-3.3 leaf stage) (22 days after treatment) | |
|---|---|---|---|
| | | Measured value | Calculated value |
| NO. 2 | 100 | 65 | — |
| Bromoxynil-octanoate | 100 | 50 | — |
| | 50 | 50 | — |
| | 25 | 40 | — |

TABLE 2-29-continued

[HYO 38]

| Compound | Active ingredient amount (g/ha) | Growth inhibition rate (%) of pricky sida (3.0-3.3 leaf stage) (22 days after treatment) | |
|---|---|---|---|
| | | Measured value | Calculated value |
| NO. 2 + bromoxynil-octanoate | 100 + 100 | 100 | 80 |
| | 100 + 50 | 100 | 80 |
| | 100 + 25 | 94 | 76 |

TABLE 2-30

[HYO 39]

| Compound | Active ingredient amount (g/ha) | Growth inhibition rate (%) of crabgrass (4.0-5.0 leaf stage) (22 days after treatment) | |
|---|---|---|---|
| | | Measured value | Calculated value |
| NO. 2 | 7 | 53 | — |
| Clopyralid | 300 | 0 | — |
| NO. 2 + clopyralid | 7 + 300 | 83 | 53 |

TABLE 2-31

[HYO 40]

| Compound | Active ingredient amount (g/ha) | Growth inhibition rate (%) of velvetleaf (4.1-4.5 leaf stage) (22 days after treatment) | |
|---|---|---|---|
| | | Measured value | Calculated value |
| NO. 2 | 7 | 60 | — |
| Clopyralid | 300 | 40 | — |
| NO. 2 + clopyralid | 7 + 300 | 88 | 76 |

TABLE 2-32

[HYO 41]

| Compound | Active ingredient amount (g/ha) | Growth inhibition rate (%) of velvetleaf (3.5 to 4.3 leaf stage) (14 days after treatment) | |
|---|---|---|---|
| | | Measured value | Calculated value |
| NO. 2 | 7 | 95 | — |
| Linuron | 250 | 85 | — |
| NO. 2 + lunuron | 7 + 250 | 100 | 99.3 |

TABLE 2-33

[HYO 42]

| Compound | Active ingredient amount (g/ha) | Growth inhibition rate (%) of crabgrass (4.0-5.0 leaf stage) (22 days after treatment) | |
|---|---|---|---|
| | | Measured value | Calculated value |
| NO. 2 | 7 | 53 | — |
| Prosulfuron | 5 | 0 | — |
| NO. 2 + prosulfuron | 7 + 5 | 89 | 53 |

TABLE 2-34

[HYO 43]

| Compound | Active ingredient amount (g/ha) | Growth inhibition rate (%) of velvetleaf (4.1-4.5 leaf stage) (22 days after treatment) | |
|---|---|---|---|
| | | Measured value | Calculated value |
| NO. 2 | 7 | 60 | — |
| Prosulfuron | 5 | 90 | — |
| NO. 2 + prosulfuron | 7 + 5 | 99 | 96 |

TABLE 2-35

[HYO 44]

| Compound | Active ingredient amount (g/ha) | Growth inhibition rate (%) of velvetleaf (3.5-4.3 leaf stage) (14 days after treatment) | |
|---|---|---|---|
| | | Measured value | Calculated value |
| NO. 2 | 7 | 95 | — |
| 2,4-D ethyl | 100 | 80 | — |
| NO. 2 + 2,4-D ethyl | 7 + 100 | 100 | 99 |

TABLE 2-36

[HYO 45]

| Compound | Active ingredient amount (g/ha) | Growth inhibition rate (%) of crabgrass (4.0-5.0 leaf stage) (22 days after treatment) | |
|---|---|---|---|
| | | Measured value | Calculated value |
| NO. 2 | 7 | 53 | — |
| Pyridate | 200 | 0 | — |
| NO. 2 + pyridate | 7 + 200 | 97 | 53 |

TABLE 2-37

[HYO 46]

| Compound | Active ingredient amount (g/ha) | Growth inhibition rate (%) of velvetleaf (4.1-4.5 leaf stage) (14 days after treatment) | |
|---|---|---|---|
| | | Measured value | Calculated value |
| NO. 2 | 7 | 70 | — |
| Pyridate | 200 | 30 | — |
| NO. 2 + pyridate | 7 + 200 | 90 | 79 |

TABLE 2-38

[HYO 47]

| Compound | Active ingredient amount (g/ha) | Growth inhibition rate (%) of crabgrass (4.4-5.0 leaf stage) (13 days after treatment) Measured value | Calculated value |
|---|---|---|---|
| NO. 2 | 5 | 65 | — |
| Dicamba | 100 | 0 | — |
| NO. 2 + dicamba | 5 + 100 | 70 | 65 |

TABLE 2-39

[HYO 48]

| Compound | Active ingredient amount (g/ha) | Growth inhibition rate (%) of velvetleaf (3.3-4.2 leaf stage) (13 days after treatment) Measured value | Calculated value |
|---|---|---|---|
| NO. 2 | 5 | 70 | — |
| Dicamba | 100 | 35 | — |
| NO. 2 + dicamba | 5 + 100 | 90 | 81 |

TABLE 2-40

[HYO 49]

| Compound | Active ingredient amount (g/ha) | Growth inhibition rate (%) of velvetleaf (3.5 to 4.3 leaf stage) (14 days after treatment) Measured value | Calculated value |
|---|---|---|---|
| NO. 2 | 15 | 97 | — |
| Glyphosate-ammonium | 100 | 30 | — |
| NO. 2 + glyphosate-ammonium | 15 + 100 | 99 | 98 |

TABLE 2-41

[HYO 50]

| Compound | Active ingredient amount (g/ha) | Growth inhibition rate (%) of crabgrass (4.0-5.0 leaf stage) (22 days after treatment) Measured value | Calculated value |
|---|---|---|---|
| NO. 2 | 7 | 53 | — |
| Glufosinate-ammonium | 100 | 0 | — |
| NO. 2 + glufosinate-ammonium | 7 + 100 | 80 | 53 |

TABLE 2-42

[HYO 51]

| Compound | Active ingredient amount (g/ha) | Growth inhibition rate (%) of velvetleaf (4.1-4.5 leaf stage) (22 days after treatment) Measured value | Calculated value |
|---|---|---|---|
| NO. 2 | 7 | 60 | — |
| Glufosinate-ammonium | 200 | 10 | — |
| NO. 2 + glufosinate-ammonium | 7 + 200 | 88 | 64 |

TABLE 2-43

[HYO 52]

| Compound | Active ingredient amount (g/ha) | Growth inhibition rate (%) of crabgrass (4.0-5.0 leaf stage) (22 days after treatment) Measured value | Calculated value |
|---|---|---|---|
| NO. 2 | 7 | 53 | — |
| Bentazone-sodium | 200 | 0 | — |
| NO. 2 + bentazone-sodium | 7 + 200 | 80 | 53 |

TABLE 2-44

[HYO 53]

| Compound | Active ingredient amount (g/ha) | Growth inhibition rate (%) of velvetleaf (4.1-4.5 leaf stage) (22 days after treatment) Measured value | Calculated value |
|---|---|---|---|
| NO. 2 | 7 | 60 | — |
| Bentazone-sodium | 100 | 0 | — |
| NO. 2 + bentazone-sodium | 7 + 100 | 100 | 60 |

TABLE 2-45

[HYO 54]

| Compound | Active ingredient amount (g/ha) | Growth inhibition rate (%) of crabgrass (4.4-5.0 leaf stage) (13 days after treatment) Measured value | Calculated value |
|---|---|---|---|
| NO. 2 | 5 | 65 | — |
| Pethoxamid | 200 | 0 | — |
| NO. 2 + pethoxamid | 5 + 200 | 70 | 65 |

TABLE 2-46

[HYO 55]

| Compound | Active ingredient amount (g/ha) | Growth inhibition rate (%) of velvetleaf (3.3-4.2 leaf stage) (13 days after treatment) | |
|---|---|---|---|
| | | Measured value | Calculated value |
| NO. 2 | 5 | 70 | — |
| Pethoxamid | 200 | 0 | — |
| NO. 2 + pethoxamid | 5 + 200 | 90 | 70 |

TABLE 2-47

[HYO 56]

| Compound | Active ingredient amount (g/ha) | Growth inhibition rate (%) of velvetleaf (3.3-4.2 leaf stage) (13 days after treatment) | |
|---|---|---|---|
| | | Measured value | Calculated value |
| NO. 2 | 5 | 70 | — |
| Pendimethalin | 100 | 25 | — |
| NO. 2 + pendimethalin | 5 + 100 | 90 | 78 |

TABLE 2-48

[HYO 57]

| Compound | Active ingredient amount (g/ha) | Growth inhibition rate (%) of crabgrass (4.4-5.0 leaf stage) (13 days after treatment) | |
|---|---|---|---|
| | | Measured value | Calculated value |
| NO. 2 | 5 | 65 | — |
| Pyroxasulfone | 50 | 0 | — |
| NO. 2 + pyroxasulfone | 5 + 50 | 70 | 65 |

TABLE 2-49

[HYO 58]

| Compound | Active ingredient amount (g/ha) | Growth inhibition rate (%) of velvetleaf (3.3-4.2 leaf stage) (13 days after treatment) | |
|---|---|---|---|
| | | Measured value | Calculated value |
| NO. 2 | 5 | 70 | — |
| Pyroxasulfone | 50 | 5 | — |
| NO. 2 + pyroxasulfone | 5 + 50 | 93 | 70 |

TABLE 2-50

[HYO 59]

| Compound | Active ingredient amount (g/ha) | Growth inhibition rate (%) of crabgrass (3.5-4.3 leaf stage) (14 days after treatment) | |
|---|---|---|---|
| | | Measured value | Calculated value |
| NO. 3 | 5 | 88 | — |
| Nicosulfuron | 5 | 15 | — |

TABLE 2-50-continued

[HYO 59]

| Compound | Active ingredient amount (g/ha) | Growth inhibition rate (%) of crabgrass (3.5-4.3 leaf stage) (14 days after treatment) | |
|---|---|---|---|
| | | Measured value | Calculated value |
| NO. 3 + nicosulfuron | 5 + 5 | 92 | 90 |

TABLE 2-51

[HYO 60]

| Compound | Active ingredient amount (g/ha) | Growth inhibition rate (%) of velvetleaf (3.1-3.4 leaf stage) (20 days after treatment) | |
|---|---|---|---|
| | | Measured value | Calculated value |
| NO. 3 | 5 | 88 | — |
| Nicosulfuron | 5 | 10 | — |
| NO. 3 + nicosulfuron | 5 + 5 | 94 | 89 |

TABLE 2-52

[HYO 61]

| Compound | Active ingredient amount (g/ha) | Growth inhibition rate (%) of prickly sida (1.54-2.4 leaf stage) (21 days after treatment) | |
|---|---|---|---|
| | | Measured value | Calculated value |
| NO. 3 | 50 | 50 | — |
| Nicosulfuron | 15 | 45 | — |
| NO. 3 + nicosulfuron | 50 + 15 | 75 | 73 |

TABLE 2-53

[HYO 62]

| Compound | Active ingredient amount (g/ha) | Growth inhibition rate (%) of days after treatment (4.0-5.0 leaf stage) (21 days after treatment) | |
|---|---|---|---|
| | | Measured value | Calculated value |
| No. 3 | 7 | 40 | — |
| Atrazine | 125 | 0 | — |
| NO. 3 + atrazine | 7 + 125 | 100 | 40 |

TABLE 2-54

[HYO 63]

| Compound | Active ingredient amount (g/ha) | Growth inhibition rate (%) of crabgrass (3.5 to 4.3 leaf stage) (14 days after treatment) | |
|---|---|---|---|
| | | Measured value | Calculated value |
| NO. 3 | 5 | 88 | — |
| Terbuthylazine | 300 | 25 | — |
| NO. 3 + terbuthylazine | 5 + 300 | 99 | 91 |

TABLE 2-55

[HYO 64]

| Compound | Active ingredient amount (g/ha) | Growth inhibition rate (%) of velvetleaf (3.1-3.4 leaf stage) (20 days after treatment) | |
|---|---|---|---|
| | | Measured value | Calculated value |
| NO. 3 | 5 | 88 | — |
| Terbuthylazine | 300 | 50 | — |
| NO. 3 + terbuthylazine | 5 + 300 | 100 | 94 |

TABLE 2-56

[HYO 65]

| Compound | Active ingredient amount (g/ha) | Growth inhibition rate (%) of prickly side (1.5-2.4 leaf stage) (20 days after treatment) | |
|---|---|---|---|
| | | Measured value | Calculated value |
| NO. 3 | 50 | 50 | — |
| Terbuthylazine | 100 | 55 | — |
| NO. 3 + terbuthylazine | 50 + 100 | 95 | 78 |

TABLE 2-57

[HYO 66]

| Compound | Active ingredient amount (g/ha) | Growth inhibition rate (%) of days after treatment (4.0-5.0 leaf stage) (21 days after treatment) | |
|---|---|---|---|
| | | Measured value | Calculated value |
| NO. 3 | 7 | 40 | — |
| Terbuthylazine | 125 | 0 | — |
| NO. 3 + terbuthylazine | 7 + 125 | 98 | 40 |

TABLE 2-58

[HYO 67]

| Compound | Active ingredient amount (g/ha) | Growth inhibition rate (%) of crabgrass (4.0-5.1 leaf stage) (21 days after treatment) | |
|---|---|---|---|
| | | Measured value | Calculated value |
| NO. 3 | 7 | 80 | — |
| Aetochlor | 150 | 0 | — |
| NO. 3 + acetochlor | 7 + 150 | 88 | 80 |

TABLE 2-59

[HYO 68]

| Compound | Active ingredient amount (g/ha) | Growth inhibition rate (%) of velvetleaf (3.1-3.4 leaf stage) (20 days after treatment) | |
|---|---|---|---|
| | | Measured value | Calculated value |
| NO. 3 | 5 | 88 | — |
| Aetochlor | 300 | 0 | — |
| NO. 3 + acetochlor | 5 + 300 | 90 | 88 |

TABLE 2-60

[HYO 69]

| Compound | Active ingredient amount (g/ha) | Growth inhibition rate (%) of crabgrass (4.0-5.1 leaf stage) (21 days after treatment) | |
|---|---|---|---|
| | | Measured value | Calculated value |
| NO. 3 | 15 | 90 | — |
| S-Metolachlor | 300 | 0 | — |
| NO. 3 + S-metolachlor | 15 + 300 | 99 | 90 |

TABLE 2-61

[HYO 70]

| Compound | Active ingredient amount (g/ha) | Growth inhibition rate (%) of velvetleaf (3.0-3.5 leaf stage) (21 days after treatment) | |
|---|---|---|---|
| | | Measured value | Calculated value |
| NO. 3 | 15 | 80 | — |
| S-Metolachlor | 300 | 0 | — |
| NO. 3 + S-metolachlor | 15 + 300 | 97 | 80 |

TABLE 2-62

[HYO 71]

| Compound | Active ingredient amount (g/ha) | Growth inhibition rate (%) of crabgrass (4.0-5.1 leaf stage) (21 days after treatment) | |
|---|---|---|---|
| | | Measured value | Calculated value |
| NO. 3 | 7 | 80 | — |
| Bromoxynil-octanoate | 63 | 0 | — |
| NO. 3 + bromoxynil-octanoate | 7 + 63 | 93 | 80 |

TABLE 2-63

[HYO 72]

| Compound | Active ingredient amount (g/ha) | Growth inhibition rate (%) of velvetleaf (3.0-3.5 leaf stage) (21 days after treatment) | |
|---|---|---|---|
| | | Measured value | Calculated value |
| NO. 3 | 7 | 60 | — |
| Bromoxynil-octanoate | 63 | 10 | — |

TABLE 2-63-continued

[HYO 72]

| Compound | Active ingredient amount (g/ha) | Growth inhibition rate (%) of velvetleaf (3.0-3.5 leaf stage) (21 days after treatment) Measured value | Calculated value |
|---|---|---|---|
| NO. 3 + bromoxynil-octanoate | 7 + 63 | 100 | 64 |

TABLE 2-64

[HYO 73]

| Compound | Active ingredient amount (g/ha) | Growth inhibition rate (%) of crabgrass (4.0-5.0 leaf stage) (16 days after treatment) Measured value | Calculated value |
|---|---|---|---|
| NO. 3 | 7 | 75 | — |
| Carfentrazone-ethyl | 15 | 0 | — |
| NO. 3 + carfentrazone-ethyl | 7 + 15 | 100 | 75 |

TABLE 2-65

[HYO 74]

| Compound | Active ingredient amount (g/ha) | Growth inhibition rate (%) of velvetleaf (3.0-3.5 leaf stage) (21 days after treatment) Measured value | Calculated value |
|---|---|---|---|
| NO. 3 | 7 | 60 | — |
| Carfentrazone-ethyl | 7 | 99 | — |
| NO. 3 + carfentrazone-ethyl | 7 + 7 | 100 | 99.6 |

TABLE 2-66

[HYO 75]

| Compound | Active ingredient amount (g/ha) | Growth inhibition rate (%) of crabgrass (4.0-5.0 leaf stage) (21 days after treatment) Measured value | Calculated value |
|---|---|---|---|
| NO. 3 | 7 | 80 | — |
| Pyroxasulfone | 50 | 10 | — |
| NO. 3 + pyroxasulfone | 7 + 50 | 95 | 82 |

TABLE 2-67

[HYO 76]

| Compound | Active ingredient amount (g/ha) | Growth inhibition rate (%) of velvetleaf (3.0-3.5 leaf stage) (21 days after treatment) Measured value | Calculated value |
|---|---|---|---|
| NO. 3 | 15 | 80 | — |
| Pyroxasulfone | 50 | 0 | — |
| NO. 3 + pyroxasulfone | 15 + 50 | 97 | 80 |

TABLE 2-68

[HYO 77]

| Compound | Active ingredient amount (g/ha) | Growth inhibition rate (%) of velvetleaf (3.5-4.3 leaf stage) (21 days after treatment) Measured value | Calculated value |
|---|---|---|---|
| NO. 3 | 3.5 | 60 | — |
| Rimsulfuron | 20 | 99 | — |
| NO. 3 + rimsulfuron | 3.5 + 20 | 100 | 99.6 |

TABLE 2-69

[HYO 78]

| Compound | Active ingredient amount (g/ha) | Growth inhibition rate (%) of velvetleaf (3.0-3.5 leaf stage) (21 days after treatment) Measured value | Calculated value |
|---|---|---|---|
| NO. 3 | 3.5 | 60 | — |
| Prosulfuron | 10 | 100 | — |
| NO. 3 + prosulfuron | 3.5 + 10 | 100 | 100 |

TABLE 2-70

[HYO 79]

| Compound | Active ingredient amount (g/ha) | Growth inhibition rate (%) of crabgrass (5.0-5.5 leaf stage) (21 days after treatment) Measured value | Calculated value |
|---|---|---|---|
| NO. 3 | 3.5 | 65 | — |
| Alachlor | 300 | 10 | — |
| NO. 3 + alachlor | 3.5 + 300 | 75 | 69 |

TABLE 2-71

[HYO 80]

| Compound | Active ingredient amount (g/ha) | Growth inhibition rate (%) of velvetleaf (3.8-4.4 leaf stage) (21 days after treatment) Measured value | Calculated value |
|---|---|---|---|
| NO. 3 | 15 | 80 | — |
| Alachlor | 300 | 0 | — |

TABLE 2-71-continued

[HYO 80]

| Compound | Active ingredient amount (g/ha) | Growth inhibition rate (%) of velvetleaf (3.8-4.4 leaf stage) (21 days after treatment) | |
|---|---|---|---|
| | | Measured value | Calculated value |
| NO. 3 + alachlor | 15 + 300 | 90 | 80 |

TABLE 2-72

[HYO 81]

| Compound | Active ingredient amount (g/ha) | Growth inhibition rate (%) of crabgrass (5.0-5.5 leaf stage) (21 days after treatment) | |
|---|---|---|---|
| | | Measured value | Calculated value |
| NO. 3 | 7 | 70 | — |
| Glyphosate-ammonium | 100 | 10 | — |
| NO. 3 + glyphosate-ammonium | 7 + 100 | 95 | 73 |

TABLE 2-73

[HYO 82]

| Compound | Active ingredient amount (g/ha) | Growth inhibition rate (%) of velvetleaf (3.5-4.3 leaf stage) (21 days after treatment) | |
|---|---|---|---|
| | | Measured value | Calculated value |
| NO. 3 | 3.5 | 60 | — |
| Glyphosate-ammonium | 200 | 15 | — |
| NO. 3 + glyphosate-ammonium | 3.5 + 200 | 73 | 66 |

TABLE 2-74

[HYO 83]

| Compound | Active ingredient amount (g/ha) | Growth inhibition rate (%) of crabgrass (5.0-5.5 leaf stage) (21 days after treatment) | |
|---|---|---|---|
| | | Measured value | Calculated value |
| NO. 3 | 7 | 70 | — |
| Dicamba | 200 | 0 | — |
| NO. 3 + dicamba | 7 + 200 | 75 | 70 |

TABLE 2-75

[HYO 84]

| Compound | Active ingredient amount (g/ha) | Growth inhibition rate (%) of velvetleaf (3.5-4.3 leaf stage) (21 days after treatment) | |
|---|---|---|---|
| | | Measured value | Calculated value |
| NO. 3 | 7 | 65 | — |
| Dicamba | 100 | 55 | — |
| NO. 3 + dicamba | 7 + 100 | 95 | 84 |

TABLE 2-76

[HYO 85]

| Compound | Active ingredient amount (g/ha) | Growth inhibition rate (%) of days after treatment (4.0-5.0 leaf stage) (14 days after treatment) | |
|---|---|---|---|
| | | Measured value | Calculated value |
| NO. 3 | 7 | 50 | — |
| Dicamba | 200 | 0 | — |
| NO. 3 + dicamba | 7 + 200 | 70 | 50 |

TABLE 2-77

[HYO 86]

| Compound | Active ingredient amount (g/ha) | Growth inhibition rate (%) of velvetleaf (3.8-4.4 leaf stage) (21 days after treatment) | |
|---|---|---|---|
| | | Measured value | Calculated value |
| NO. 4 | 15 | 75 | — |
| Nicosulfuron | 7 | 30 | — |
| NO. 4 + nicosulfuron | 15 + 7 | 97 | 83 |

TABLE 2-78

[HYO 87]

| Compound | Active ingredient amount (g/ha) | Growth inhibition rate (%) of velvetleaf (3.3-3.8 leaf stage) (22 days after treatment) | |
|---|---|---|---|
| | | Measured value | Calculated value |
| NO. 4 | 15 | 89 | — |
| Nicosulfuron | 30 | 70 | — |
| | 15 | 60 | — |
| | 7 | 45 | — |
| | 3.5 | 40 | — |
| NO. 4 + nicosulfuron | 15 + 30 | 98 | 97 |
| | 15 + 15 | 99 | 96 |
| | 15 + 7 | 97 | 94 |
| | 15 + 3.5 | 99 | 93 |

TABLE 2-79

[HYO 88]

| Compound | Active ingredient amount (g/ha) | Growth inhibition rate (%) of prickly sida (1.5-2.4 leaf stage) (20 days after treatment) | |
|---|---|---|---|
| | | Measured value | Calculated value |
| NO. 4 | 75 | 55 | — |
| Nicosulfuron | 15 | 45 | — |
| NO. 4 + nicosulfuron | 75 + 15 | 83 | 75 |

TABLE 2-80

[HYO 89]

| Compound | Active ingredient amount (g/ha) | Growth inhibition rate (%) of crabgrass (4.0-4.5 leaf stage) (14 days after treatment) | |
|---|---|---|---|
| | | Measured value | Calculated value |
| NO. 4 | 15 | 70 | — |
| Atrazine | 800 | 40 | — |
| | 400 | 30 | — |
| | 50 | 20 | — |
| NO. 4 + atrazine | 15 + 800 | 85 | 82 |
| | 15 + 400 | 83 | 79 |
| | 15 + 50 | 80 | 76 |

TABLE 2-81

[HYO 90]

| Compound | Active ingredient amount (g/ha) | Growth inhibition rate (%) of velvetleaf (3.1-3.5 leaf stage) (20 days after treatment) | |
|---|---|---|---|
| | | Measured value | Calculated value |
| NO. 4 | 3.5 | 68 | — |
| Atrazine | 800 | 100 | — |
| | 600 | 80 | — |
| | 400 | 40 | — |
| | 200 | 35 | 00 |
| | 100 | 30 | — |
| | 50 | 30 | |
| NO. 4 + atrazine | 3.5 + 800 | 100 | 100 |
| | 3.5 + 600 | 100 | 94 |
| | 3.5 + 400 | 100 | 81 |
| | 3.5 + 200 | 93 | 79 |
| | 3.5 + 100 | 100 | 78 |
| | 3.5 + 50 | 100 | 78 |

TABLE 2-82

[HYO 91]

| Compound | Active ingredient amount (g/ha) | Growth inhibition rate (%) of days after treatment (4.0-5.0 leaf stage) (8 days after treatment) | |
|---|---|---|---|
| | | Measured value | Calculated value |
| No. 4 | 7 | 65 | — |
| Atrazine | 250 | 10 | — |
| NO. 4 + atrazine | 7 + 250 | 95 | 69 |

TABLE 2-83

[HYO 92]

| Compound | Active ingredient amount (g/ha) | Growth inhibition rate (%) of crabgrass (3.5-4.3 leaf stage) (14 days after treatment) | |
|---|---|---|---|
| | | Measured value | Calculated value |
| NO. 4 | 5 | 90 | — |
| Terbuthylazine | 300 | 25 | — |
| NO. 4 + terbuthylazine | 5 + 300 | 99 | 93 |

TABLE 2-84

[HYO 93]

| Compound | Active ingredient amount (g/ha) | Growth inhibition rate (%) of velvetleaf (3.1-3.4 leaf stage) (21 days after treatment) | |
|---|---|---|---|
| | | Measured value | Calculated value |
| NO. 4 | 5 | 94 | — |
| Terbuthylazine | 300 | 50 | — |
| NO. 4 + terbuthylazine | 5 + 300 | 100 | 97 |

TABLE 2-85

[HYO 94]

| Compound | Active ingredient amount (g/ha) | Growth inhibition rate (%) of prickly sida (1.5-2.4 leaf stage) (20 days after treatment) | |
|---|---|---|---|
| | | Measured value | Calculated value |
| NO. 4 | 75 | 55 | — |
| Terbuthylazine | 100 | 55 | — |
| NO. 4 + terbuthylazine | 75 + 100 | 93 | 80 |

TABLE 2-86

[HYO 95]

| Compound | Active ingredient amount (g/ha) | Growth inhibition rate (%) of days after treatment (4.0-5.0 leaf stage) (8 days after treatment) | |
|---|---|---|---|
| | | Measured value | Calculated value |
| NO. 4 | 7 | 65 | — |
| Terbuthylazine | 250 | 10 | — |
| NO. 4 + terbuthylazine | 7 + 250 | 100 | 69 |

TABLE 2-87

[HYO 96]

| Compound | Active ingredient amount (g/ha) | Growth inhibition rate (%) of crabgrass (4.0-5.0 leaf stage) (14 days after treatment) | |
|---|---|---|---|
| | | Measured value | Calculated value |
| NO. 4 | 7 | 60 | — |
| Acetochlor | 150 | 0 | — |

TABLE 2-87-continued

[HYO 96]

| Compound | Active ingredient amount (g/ha) | Growth inhibition rate (%) of crabgrass (4.0-5.0 leaf stage) (14 days after treatment) | |
|---|---|---|---|
| | | Measured value | Calculated value |
| NO. 4 + acetochlor | 7 + 150 | 75 | 60 |

TABLE 2-88

[HYO 97]

| Compound | Active ingredient amount (g/ha) | Growth inhibition rate (%) of crabgrass (3.5-5.0 leaf stage) (7 days after treatment) | |
|---|---|---|---|
| | | Measured value | Calculated value |
| NO.4 | 3.5 | 65 | — |
| Acetochlor | 750 | 10 | — |
| | 500 | 0 | — |
| | 250 | 0 | — |
| | 125 | 0 | — |
| | 63 | 0 | — |
| NO. 4 + acetochlor | 3.5 + 750 | 73 | 69 |
| | 3.5 + 500 | 70 | 65 |
| | 3.5 + 250 | 70 | 65 |
| | 3.5 + 125 | 70 | 65 |
| | 3.5 + 63 | 70 | 65 |

TABLE 2-89

[HYO 98]

| Compound | Active ingredient amount (g/ha) | Growth inhibition rate (%) of velvetleaf (3.0-4.0 leaf stage) (14 days after treatment) | |
|---|---|---|---|
| | | Measured value | Calculated value |
| NO. 4 | 7 | 70 | — |
| Acetochlor | 150 | 0 | — |
| NO. 4 + acetochlor | 7 + 150 | 78 | 70 |

TABLE 2-90

[HYO 99]

| Compound | Active ingredient amount (g/ha) | Growth inhibition rate (%) of velvetleaf (2.3-3.5 leaf stage) (7 days after treatment) | |
|---|---|---|---|
| | | Measured value | Calculated value |
| NO. 4 | 3.5 | 70 | — |
| Acetochlor | 750 | 0 | — |
| | 500 | 10 | — |
| | 250 | 0 | — |
| | 125 | 0 | — |
| | 63 | 0 | — |
| NO. 4 + acetochlor | 3.5 + 750 | 73 | 70 |
| | 3.5 + 250 | 73 | 70 |
| | 3.5 + 63 | 73 | 70 |

TABLE 2-91

[HYO 100]

| Compound | Active ingredient amount (g/ha) | Growth inhibition rate (%) of crabgrass (4.0-5.0 leaf stage) (14 days after treatment) | |
|---|---|---|---|
| | | Measured value | Calculated value |
| NO. 4 | 7 | 60 | — |
| S-Metolachlor | 150 | 0 | — |
| NO. 4 + S-metolachlor | 7 + 150 | 70 | 60 |

TABLE 2-92

[HYO 101]

| Compound | Active ingredient amount (g/ha) | Growth inhibition rate (%) of velvetleaf (3.0-4.0 leaf stage) (14 days after treatment) | |
|---|---|---|---|
| | | Measured value | Calculated value |
| NO. 4 | 15 | 73 | — |
| | 150 | 0 | — |
| NO. 4 + S-metolachlor | 15 + 150 | 83 | 73 |

TABLE 2-93

[HYO 102]

| Compound | Active ingredient amount (g/ha) | Growth inhibition rate (%) of crabgrass (4.0-5.0 leaf stage) (14 days after treatment) | |
|---|---|---|---|
| | | Measured value | Calculated value |
| NO. 4 | 7 | 60 | — |
| Bromoxynil-octanoate | 63 | 0 | — |
| NO. 4 + Bromoxynil-octanoate | 7 + 63 | 80 | 60 |

TABLE 2-94

[HYO 103]

| Compound | Active ingredient amount (g/ha) | Growth inhibition rate (%) of velvetleaf (3.2-4.1 leaf stage) (24 days after treatment) | |
|---|---|---|---|
| | | Measured value | Calculated value |
| NO. 4 | 7 | 60 | — |
| Bromoxynil-octanoate | 200 | 100 | — |
| NO. 4 + Bromoxynil-octanoate | 7 + 200 | 100 | 100 |

TABLE 2-95

[HYO 104]

| Compound | Active ingredient amount (g/ha) | Growth inhibition rate (%) of crabgrass (4.0-5.0 leaf stage) (14 days after treatment) | |
|---|---|---|---|
| | | Measured value | Calculated value |
| NO. 4 | 7 | 60 | — |
| Carfentrazone-ethyl | 15 | 5 | — |
| NO. 4 + carfentrazone-ethyl | 7 + 15 | 70 | 62 |

TABLE 2-96

[HYO 105]

| Compound | Active ingredient amount (g/ha) | Growth inhibition rate (%) of velvetleaf (3.0-4.0 leaf stage) (14 days after treatment) | |
|---|---|---|---|
| | | Measured value | Calculated value |
| NO. 4 | 15 | 80 | — |
| Carfentrazone-ethyl | 15 | 98 | — |
| NO. 4 + carfentrazone-ethyl | 15 + 15 | 100 | 99.6 |

TABLE 2-97

[HYO 106]

| Compound | Active ingredient amount (g/ha) | Growth inhibition rate (%) of crabgrass (4.0-5.0 leaf stage) (14 days after treatment) | |
|---|---|---|---|
| | | Measured value | Calculated value |
| NO. 4 | 7 | 60 | — |
| Pyroxasulfone | 100 | 5 | — |
| NO. 4 + pyroxasulfone | 7 + 1-- | 75 | 62 |

TABLE 2-98

[HYO 107]

| Compound | Active ingredient amount (g/ha) | Growth inhibition rate (%) of velvetleaf (3.0-4.0 leaf stage) (14 days after treatment) | |
|---|---|---|---|
| | | Measured value | Calculated value |
| NO. 4 | 15 | 73 | — |
| Pyroxasulfone | 50 | 0 | — |
| NO. 4 + pyroxasulfone | 15 + 50 | 89 | 73 |

TABLE 2-99

[HYO 108]

| Compound | Active ingredient amount (g/ha) | Growth inhibition rate (%) of crabgrass (4.0-5.1 leaf stage) (23 days after treatment) | |
|---|---|---|---|
| | | Measured value | Calculated value |
| NO. 4 | 7 | 80 | — |
| Flufenacet | 300 | 0 | — |

TABLE 2-99-continued

[HYO 108]

| Compound | Active ingredient amount (g/ha) | Growth inhibition rate (%) of crabgrass (4.0-5.1 leaf stage) (23 days after treatment) | |
|---|---|---|---|
| | | Measured value | Calculated value |
| NO. 4 + flufenacet | 7 + 300 | 95 | 80 |

TABLE 2-100

[HYO 109]

| Compound | Active ingredient amount (g/ha) | Growth inhibition rate (%) of velvetleaf (3.0 to 3.5 leaf stage) (23 days after treatment) | |
|---|---|---|---|
| | | Measured value | Calculated value |
| NO. 4 | 15 | 93 | — |
| Flufenacet | 300 | 0 | — |
| NO. 4 + flufenacet | 15 + 300 | 98 | 93 |

TABLE 2-101

[HYO 110]

| Compound | Active ingredient amount (g/ha) | Growth inhibition rate (%) of crabgrass (4.0-5.1 leaf stage) (23 days after treatment) | |
|---|---|---|---|
| | | Measured value | Calculated value |
| NO. 4 | 15 | 85 | — |
| Clopyralid | 300 | 0 | — |
| NO. 4 + clopyralid | 15 + 300 | 98 | 85 |

TABLE 2-102

[HYO 111]

| Compound | Active ingredient amount (g/ha) | Growth inhibition rate (%) of velvetleaf (3.0-3.5 leaf stage) (23 days after treatment) | |
|---|---|---|---|
| | | Measured value | Calculated value |
| NO. 4 | 7 | 75 | — |
| Clopyralid | 300 | 35 | — |
| NO. 4 + clopyralid | 7 + 300 | 98 | 84 |

TABLE 2-103

[HYO 112]

| Compound | Active ingredient amount (g/ha) | Growth inhibition rate (%) of crabgrass (4.0-5.1 leaf stage) (23 days after treatment) | |
|---|---|---|---|
| | | Measured value | Calculated value |
| NO. 4 | 15 | 85 | — |
| Bentazone-sodium | 200 | 0 | — |
| NO. 4 + bentazone-sodium | 15 + 2-- | 90 | 85 |

TABLE 2-104

[HYO 113]

| Compound | Active ingredient amount (g/ha) | Growth inhibition rate (%) of velvetleaf (3.0-3.5 leaf stage) (23 days after treatment) | |
|---|---|---|---|
| | | Measured value | Calculated value |
| NO. 4 | 7 | 75 | — |
| Bentazone-sodium | 200 | 30 | — |
| NO. 4 + bentazone-sodium | 7 + 200 | 99 | 83 |

TABLE 2-105

[HYO 114]

| Compound | Active ingredient amount (g/ha) | Growth inhibition rate (%) of crabgrass (5.0-5.5 leaf stage) (14 days after treatment) | |
|---|---|---|---|
| | | Measured value | Calculated value |
| NO. 4 | 7 | 75 | — |
| Linuron | 250 | 30 | — |
| NO. 4 + linuron | 7 + 250 | 90 | 83 |

TABLE 2-106

[HYO 115]

| Compound | Active ingredient amount (g/ha) | Growth inhibition rate (%) of velvetleaf (3.2-4.1 leaf stage) (24 days after treatment) | |
|---|---|---|---|
| | | Measured value | Calculated value |
| NO. 4 | 7 | 60 | — |
| Linuron | 250 | 40 | — |
| NO. 4 + bentazone-sodium | 7 + 250 | 100 | 76 |

TABLE 2-107

[HYO 116]

| Compound | Active ingredient amount (g/ha) | Growth inhibition rate (%) of crabgrass (4.0-5.1 leaf stage) (23 days after treatment) | |
|---|---|---|---|
| | | Measured value | Calculated value |
| NO. 4 | 7 | 80 | — |
| Rimsulfuron | 15 | 98 | — |
| NO. 4 + rimsulfuron | 7 + 15 | 100 | 99.6 |

TABLE 2-108

[HYO 117]

| Compound | Active ingredient amount (g/ha) | Growth inhibition rate (%) of velvetleaf (3.0-3.5 leaf stage) (23 days after treatment) | |
|---|---|---|---|
| | | Measured value | Calculated value |
| NO. 4 | 7 | 75 | — |
| Rimsulfuron | 15 | 70 | — |

TABLE 2-108-continued

[HYO 117]

| Compound | Active ingredient amount (g/ha) | Growth inhibition rate (%) of velvetleaf (3.0-3.5 leaf stage) (23 days after treatment) | |
|---|---|---|---|
| | | Measured value | Calculated value |
| NO. 4 + rimsulfuron | 7 + 15 | 99 | 93 |

TABLE 2-109

[HYO 118]

| Compound | Active ingredient amount (g/ha) | Growth inhibition rate (%) of crabgrass (4.0-5.1 leaf stage) (23 days after treatment) | |
|---|---|---|---|
| | | Measured value | Calculated value |
| NO. 4 | 15 | 85 | — |
| Prosulfuron | 10 | 0 | — |
| NO. 4 + prosulfuron | 15 + 10 | 90 | 85 |

TABLE 2-110

[HYO 119]

| Compound | Active ingredient amount (g/ha) | Growth inhibition rate (%) of crabgrass (5.0-5.5 leaf stage) (14 days after treatment) | |
|---|---|---|---|
| | | Measured value | Calculated value |
| NO. 4 | 3.5 | 60 | — |
| Halofulfuron-methyl | 20 | 0 | — |
| NO. 4 + halosulfuron-methyl | 3.5 + 20 | 65 | 60 |

TABLE 2-111

[HYO 120]

| Compound | Active ingredient amount (g/ha) | Growth inhibition rate (%) of days after treatment (4.0-5.0 leaf stage) (21 days after treatment) | |
|---|---|---|---|
| | | Measured value | Calculated value |
| NO. 4 | 7 | 60 | — |
| Thifensulfuron-methyl | 5 | 0 | — |
| NO. 4 + thifensulfuron-methyl | 7 + 5 | 75 | 60 |

TABLE 2-112

[HYO 121]

| Compound | Active ingredient amount (g/ha) | Growth inhibition rate (%) of giant foxtail (4.0-5.0 leaf stage) (14 days after treatment) | |
|---|---|---|---|
| | | Measured value | Calculated value |
| NO. 4 | 7 | 75 | — |
| Thifensulfuron-methyl | 5 | 0 | — |
| NO. 4 + thifensulfuron-methyl | 7 + 5 | 80 | 75 |

TABLE 2-113

[HYO 122]

| Compound | Active ingredient amount (g/ha) | Growth inhibition rate (%) of velvetleaf (4.0-4.3 leaf stage) (21 days after treatment) | |
|---|---|---|---|
| | | Measured value | Calculated value |
| NO. 4 | 3.5 | 40 | — |
| 2,4-D ethyl | 125 | 85 | — |
| NO. 4 + 2,4-D ethyl | 3.5 + 125 | 100 | 91 |

TABLE 2-114

[HYO 123]

| Compound | Active ingredient amount (g/ha) | Growth inhibition rate (%) of velvetleaf (3.2-4.1 leaf stage) (24 days after treatment) | |
|---|---|---|---|
| | | Measured value | Calculated value |
| NO. 4 | 7 | 60 | — |
| Glufosinate-ammonium | 200 | 30 | — |
| NO. 4 + glufosinate-ammonium | 7 + 200 | 93 | 72 |

TABLE 2-115

[HYO 124]

| Compound | Active ingredient amount (g/ha) | Growth inhibition rate (%) of velvetleaf (3.2-4.1 leaf stage) (24 days after treatment) | |
|---|---|---|---|
| | | Measured value | Calculated value |
| NO. 4 | 7 | 60 | — |
| Mesotrione | 15 | 88 | — |
| NO. 4 + mesotrione | 7 + 15 | 99 | 95 |

TABLE 2-116

[HYO 125]

| Compound | Active ingredient amount (g/ha) | Growth inhibition rate (%) of days after treatment (4.0-5.0 leaf stage) (21 days after treatment) | |
|---|---|---|---|
| | | Measured value | Calculated value |
| NO. 4 | 3.5 | 40 | — |
| Mesotrione | 15 | 5 | — |
| NO. 4 + mesotrione | 3.5_15 | 50 | 43 |

TABLE 2-117

[HYO 126]

| Compound | Active ingredient amount (g/ha) | Growth inhibition rate (%) of velvetleaf (3.2-4.1 leaf stage) (24 days after treatment) | |
|---|---|---|---|
| | | Measured value | Calculated value |
| NO. 4 | 15 | 93 | — |
| Sulcotrione | 31 | 60 | — |

TABLE 2-117-continued

[HYO 126]

| Compound | Active ingredient amount (g/ha) | Growth inhibition rate (%) of velvetleaf (3.2-4.1 leaf stage) (24 days after treatment) | |
|---|---|---|---|
| | | Measured value | Calculated value |
| NO. 4 + sulcotrione | 15 + 31 | 99 | 97 |

TABLE 2-118

[HYO 127]

| Compound | Active ingredient amount (g/ha) | Growth inhibition rate (%) of days after treatment (4.0-5.0 leaf stage) (21 days after treatment) | |
|---|---|---|---|
| | | Measured value | Calculated value |
| NO. 4 | 7 | 60 | — |
| Pyridate | 100 | 0 | — |
| NO. 4 + pyridate | 7 + 100 | 93 | 60 |

TABLE 2-119

[HYO 128]

| Compound | Active ingredient amount (g/ha) | Growth inhibition rate (%) of fiant foxtail (4.0-5.0 leaf stage) (14 days after treatment) | |
|---|---|---|---|
| | | Measured value | Calculated value |
| NO. 4 | 7 | 75 | — |
| Pyridate | 100 | 0 | — |
| NO. 4 + pyridate | 7 + 100 | 80 | 75 |

The invention claimed is:

1. A synergistic herbicidal composition, comprising, as active ingredients:

a herbicidal benzoylpyrazole compound 1-(1-ethyl-4-(3-(2-methoxyethoxy)-2-methyl-4-(methylsulfonyl)benzoyl)-1H-pyrazol-5-yloxy)ethyl methyl carbonate or its salt, and at least one other herbicidal compound selected from the group consisting of hexazinone, metribuzin, cyanazine, cybutryne, triaziflam, indaziflam, metamitron, diflufenican, bicyclopyrone, quizalofop-ethyl, quizalofop-P, quizalofop-P-ethyl, quizalofop-P-tefuryl, fenoxaprop-ethyl, fenoxaprop-P, fenoxaprop-P-ethyl, metamifop-propyl, metamifop, propaquizafop, chlorimuron-ethyl, chlorimuron, sulfometuron-methyl, sulfometuron, primisulfuron-methyl, primisulfuron, bensulfuron-methyl, bensulfuron, cyclosulfamuron, ethoxysulfuron, oxasulfuron, foramsulfuron, mesosulfuron-methyl, mesosulfuron, orthosulfamuron, and amidosulfuron wherein the herbicidal benzoylpyrazole compound and the at least one other herbicide compound is present in a synergistically effective amount.

2. The synergistic herbicidal composition according to claim 1, wherein a mixing ratio of the herbicidal benzopyrazole compound or its salt to the at least one other herbicidal compound is from 1:1500 to 100:1 by weight.

3. The synergistic herbicidal composition according to claim 2, wherein the mixing ratio is from 1:1200 to 30:1 by weight.

4. A method for controlling undesired plants, the method comprising:
applying an herbicidally effective amount of the synergistic herbicidal composition of claim 1 to an undesired plant in need thereof of or to a place where an undesired plant in need thereof grows.

5. The method of claim 4, further comprising:
applying at least one selected from the group consisting of a fungicide, an antibiotic, a plant hormone, and an insecticide to the undesired plant or to the place where the undesired plant grows.

6. A synergistic method for controlling undesired plants, the method comprising:
applying an herbicidally effective amount of 1-(1-ethyl-4-(3-(2-methoxyethoxy)-2-methyl-4-(methylsulfonyl)benzoyl)-1H-pyrazol-5-yloxy)ethyl methyl carbonate or its salt as an herbicidal benzoylpyrazole compound and at least one other herbicidal compound to an undesired plant in need thereof or to a place where an undesired plant in need thereof grows,
wherein the at least one other herbicidal compound is selected from the group consisting of hexazinone, metribuzin, cyanazine, cybutryne, triaziflam, indaziflam, metamitron, diflufenican bicyclopyrone, quizalofop-ethyl, quizalofop-P, quizalofop-P-ethyl, quizalofop-P-tefuryl, fenoxaprop-ethyl, fenoxaprop-P, fenoxaprop-P-ethyl, metamifop-propyl, metamifop, propaquizafop, chlorimuron-ethyl, chlorimuron, sulfometuron-methyl, sulfometuron, primisulfuron-methyl, primisulfuron, bensulfuron-methyl, bensulfuron, cyclosulfamuron, ethoxysulfuron, oxasulfuron, foramsulfuron, mesosulfuron-methyl, mesosulfuron, orthosulfamuron, and amidosulfuron wherein the herbicidal benzoylpyrazole compound and the at least one other herbicide compound is present in a synergistically effective amount.

7. The synergistic method of claim 6, further comprising:
applying at least one selected from the group consisting of a fungicide, an antibiotic, a plant hormone, and an insecticide to the undesired plant or to the place where the undesired plant grows.

8. The synergistic herbicidal composition of claim 1, wherein the at least one other herbicidal compound is at least one compound selected from the group consisting of metribuzin, metamitron, diflufenican, bicyclopyrone, quizalofop-ethyl, quizalofop-P, quizalofop-P-ethyl, quizalofop-P-tefuryl, fenoxaprop-ethyl, fenoxaprop-P, fenoxaprop-P-ethyl, metamifop-propyl, metamifop, propaquizafop, chlorimuron-ethyl, chlorimuron, sulfometuron-methyl, sulfometuron, primisulfuron-methyl, primisulfuron, bensulfuron-methyl, bensulfuron, oxasulfuron, foramsulfuron, mesosulfuron-methyl, mesosulfuron, and orthosulfamuron.

9. The synergistic herbicidal composition of claim 1, wherein the at least one other herbicidal compound is at least one compound selected from the group consisting of metribuzin, diflufenican, bicyclopyrone, quizalofop-ethyl, quizalofop-P, quizalofop-P-ethyl, quizalofop-P-tefuryl, fenoxaprop-ethyl, fenoxaprop-P, fenoxaprop-P-ethyl, metamifop-propyl, metamifop, primisulfuron-methyl, primisulfuron, and foramsulfuron.

* * * * *

UNITED STATES PATENT AND TRADEMARK OFFICE
CERTIFICATE OF CORRECTION

PATENT NO. : 8,846,571 B2  
APPLICATION NO. : 13/910562  
DATED : September 30, 2014  
INVENTOR(S) : Hiroshi Kikugawa et al.

Page 1 of 1

It is certified that error appears in the above-identified patent and that said Letters Patent is hereby corrected as shown below:

On the title page, item 72, change the residence of Inventor Hiroshi Kikugawa from "Kusatasu (JP);" to --Kusatsu (JP);--

Signed and Sealed this  
Sixteenth Day of June, 2015

Michelle K. Lee  
*Director of the United States Patent and Trademark Office*